United States Patent [19]
Yang et al.

[11] Patent Number: 5,192,525
[45] Date of Patent: Mar. 9, 1993

[54] HIGH AFFINITY TAMOXIFEN DERIVATIVES AND USES THEREOF

[75] Inventors: David J. Yang, Sugarland; Sidney Wallace, Houston, both of Tex.

[73] Assignee: Board of Regents, The University of Texas System, Austin, Tex.

[21] Appl. No.: 722,322

[22] Filed: Jun. 28, 1991

Related U.S. Application Data

[63] Continuation-in-part of Ser. No. 589,928, Oct. 1, 1990.

[51] Int. Cl.[5] ...................... A61K 49/02; A61K 43/00
[52] U.S. Cl. ..................................... 424/1.1; 128/659
[58] Field of Search ................ 424/1.1; 514/648, 651, 514/874; 564/324; 128/659

[56] References Cited

U.S. PATENT DOCUMENTS 3,288,806  11/1966  DeWald ............................. 548/575
4,696,949   9/1987  Tiovola .............................. 514/648
4,839,155   6/1989  McCague ........................... 424/1.1

FOREIGN PATENT DOCUMENTS 0054168  6/1982  European Pat. Off. .
0260066  3/1988  European Pat. Off. .

OTHER PUBLICATIONS

International Search Report (1992).
Watanabe et al. (1989) Journal of Chromatography, 497:169-180.
D'Argy et al. (1989) Chemical Abstracts, 110(3):259, Abstract No. 20581h.
Kangus et al. (1989) Chemical Abstracts, 110(25):10, Abstract No. 224948t.
Hannu et al. (1990) Chemical Abstracts, 113(17):Abstract No. 144793k.
Pomper et al. (1988), J. Med Chem., 31:1360-1363.
Armstrong (1987), Journal of Chromatography, 414:492-196.
Lien et al. (1987), Clin. Chem. 33(9):1608-1614.
Yang et al. (1991), Pharmaceutical Research, 8(2):174-177.
Shani et al. (1979), Cancer Treat Rep. (U.S.A.), 63(7):Abstract Number 366.
Shani et al. (1985), J. Med. Chem. 28:1504-1511.
Mintun et al. (1988), Radiology, 169:45-48.
Foster et al. (1985), J. Med. Chem. 28(10):1491-1497.
Kangas et al. (1986), Cancer Chemother Pharmacol 17:109-113.
DeGregorio et al. (1989), Cancer Chemother Pharmacol 23:68-70.
DeGregorio et al. (1987), Cancer Chemother Pharmacol 20:361-381.
Kallio et al. (1986), Cancer Chemother Pharmacol 17:103-108.

(List continued on next page.)

Primary Examiner—Robert L. Stoll
Assistant Examiner—John M. Covert
Attorney, Agent, or Firm—Arnold, White & Durkee

[57] ABSTRACT

The synthesis of tamoxifen derivatives, most particularly halo, haloalkyl and hydroxy tamoxifen derivatives, wherein the native tamoxifen molecule includes a substituted chemical group positioned on the aliphatic chain of the tamoxifen molecule, is provided. Methods for imaging estrogen receptors using the tamoxifen derivatives of the invention are also described. The aliphatic chain substituted tamoxifen derivatives of the invention possess greater estrogen receptor binding affinities and more potent tumor cell inhibiting activity than native tamoxifen or tamoxifen derivatives substituted at other locations on the molecule (i.e., non-aliphatic chain substituted tamoxifen, phenolic-ring substituted tamoxifen). Examples of the halogenated tamoxifen derivatives of the invention include chloro-, bromo-, iodo- and fluoro-tamoxifen derivatives, and their corresponding lower alkyl halogenated forms.

10 Claims, 10 Drawing Sheets

OTHER PUBLICATIONS

Robertson et al. (1982), *J. Org. Chem.* 47:2387–2393.
Katzenellenbogen et al. (1984), *Cancer Research* 44:112–119.
Kuroda, et al. (1985), *J. Med. Chem* 28:1497–1503.
Ram et al. (1989), *Journal of Labelled Compounds and Radiopharmaceuticals*, 27(6):661–668.
Hanson et al. (1982), *Int. J. Nucl. Med. Biol.*, 9:105–107.
Ram et al. (1988), *Journal of Labelled Compounds and Radiopharmaceuticals*, 28(6):661–668.
Loser et al. (1985), *Eur. J. Cancer Clip. Oncol.*, 21(8):985–990.
Yang et al. (Jun. 11, 1991), *The Society of Nuclear Medicine 38th Annual Meeting Cincinnati Convention Center*, No. 12071.
Tansey et al. (Jun. 11, 1991), *The Society of Nuclear Medicine 38th Annual Meeting Cincinnati Convention Center*, No. 32680.
Yang et al. (Jun. 30, 1992).
Foster et al. (1986) *Anti-Cancer Drug Design*, 1:245–257.
Francesco et al. (1986) *Steroids*, 48(5–6):287–313.

HIGH AFFINITY TAMOXIFEN DERIVATIVES AND USES THEREOF

The present application is a continuation-in-part application of Applicant's co-pending application, filed Oct. 1, 1990, U.S. Ser. No. 07/589,928, now pending. Applicants hereby claim priority to this earlier filed application. The Specification of U.S. Ser. No. 07/589,928 is specifically incorporated herein by reference.

BACKGROUND OF THE INVENTION

1. Field of the Invention

The present invention relates to the field of tamoxifen derivatives and analogs, particularly halogenated tamoxifen derivatives and analogs. In that novel tamoxifen derivatives are described wherein the aliphatic chain of the molecule is substituted with a halogen group, the present invention also relates to methods of synthesizing tamoxifen analogs and derivatives.

In that the described tamoxifen derivatives have high affinity for binding estrogen receptors and may be labeled with detectable "tagging" molecules, rendering labeled estrogen receptors highly visible through positron emission tomography (PET) and single photon emission computed tomography (SPECT), the present invention also relates to reagents, radiopharmaceuticals and techniques in the field of molecular imaging.

The halogenated tamoxifen derivatives of the present invention are advantageously used in the imaging of estrogen receptors, for example, in breast, ovarian, uterine and brain tissue and may therefore be useful in the diagnosis of estrogen-receptor positive cancers.

The present invention also relates to the field of anti-cancer therapeutic agents, particularly to methods of breast tumor therapy, in that the described high affinity of these halogenated (i.e., iodo-, fluoro-, bromo- and chloro-) tamoxifen derivatives for estrogen receptors may be advantageously used to treat estrogen-receptor positive tumors.

2. Background of the Invention

Endocrine therapy provides an important nonsurgical method for treatment for breast carcinoma. This type of therapy is still considered standard for certain subsets of patients, typically postmenopausal women whose primary tumors have high estrogen levels.[1-3] The synthesis of F-18 fluoroestradiol for application in diagnosing breast tumors in humans has recently been described.[4] Observation of significant changes in the binding of estrogen receptors in breast tumors were reported using PET. However, technical difficulties associated with estrogen receptor saturation in patients receiving tamoxifen, or other estrogen receptor antagonist, has been observed to decrease the sensitivity and accuracy of using an estrogen-based receptor tag in diagnosing and monitoring the progress of tumors in patients receiving such treatments.

Tamoxifen (I), a potent non-steroidal antiestrogen, has been widely used in the treatment of human breast tumors. Tamoxifen has few side effects when compared with other hormonal treatments. Tamoxifen is cytostatic (i.e, it prevents/inhibits cell growth), and exerts competitive inhibitory activity at the receptor level with estrogen. More specifically, the cytostatic activity of tamoxifen results from its ability to bind to cytoplasmic estrogen receptors and be translocated to cell nuclei, where cell proliferation is prevented.[1-3] Thus, tamoxifen is often administered as an anticancer agent.[6] For example, Foster et al.[6] describes the effect of various tamoxifen hydroxy-derivatives on the growth of MCF-7 breast cancer cell line in its native form. However, highly active in vitro hydroxy tamoxifen derivatives were found to be less active than tamoxifen in vivo against a DMBA-induced ER-positive tumor in rats and only slightly more active against a hormone dependent mammary tumor in mice.

Tamoxifen has a relatively low binding affinity for the estrogen receptor (ER). Attempts have therefore been made to synthesize tamoxifen derivatives having improved ER binding affinity and specificity to enhance its action as an anti-cancer therapeutic agent. The structure of tamoxifen is demonstrated as:

[Formula 1]

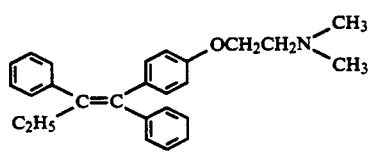

A variety of modified tamoxifen derivatives have been described in the literature. Structural modifications have been made at virtually every site on the three aromatic rings of the tamoxifen molecule. For example, a 4-hydroxytamoxifen derivative in which $X = -OH$ has been developed having the structure shown below[33]:

[Formula 2]

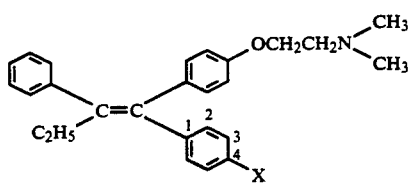

However, while the 4-hydroxytamoxifen derivative was shown to be a potent anti-estrogen in vitro, it proved to be less effective than tamoxifen in vivo, owing to rapid glucuronidation of the hydroxyl group, followed by excretion. 4-Hydroxytamoxifen is the active intracellular form of the tamoxifen molecule in vivo, due to cytoplasmic hydroxylation after tamoxifen enters the cell. However, when 4-hydroxytamoxifen is administered in vivo, its polarity reduces its ability to cross the cell membrane, thereby reducing its access to estrogen receptors located in the cytoplasm. Therefore, in vivo tests indicate 4-hydroxytamoxifen to be less active than the native tamoxifen.[23]

Other tamoxifen derivatives having a 4-position substitution of the phenyl ring, in which X is methoxy, methyl, fluoro or chloro, have also been proposed and evaluated.[15] K. E. Allen et al. (1980) conducted studies wherein the 4-methyl, 4-chloro and 4-fluoro derivatives were evaluated and found to have approximately equal activity for estrogen receptor binding affinity compared to tamoxifen in vitro. However, uterine weight tests indicated that these phenyl group derivatives had lower anti-estrogenic activity than tamoxifen, while other tests indicated that the activity of the 4-methoxy phenyl derivative was about the same as native tamoxifen.

A 4-iodo substitution of the phenyl ring as a tamoxifen derivative (formula 2: X=iodo) has recently been found to have greater potency than tamoxifen in relation to detecting estrogen receptor-positive breast cancer.[13] Other 3-iodo, 4-iodo, 3-bromo and 4-bromo phenyl ring-substituted tamoxifen derivatives have also been described.[13] For example, the McCaque et al. patent (U.S. Pat. No. 4,839,155) described the preparation of an iodo or bromo halogenated tamoxifen. However, the halogen, I or Br, was again substituted at one of the phenyl rings of the tamoxifen structure.

Derivatives of tamoxifen wherein other than the phenyl groups of the molecule are substituted have not been proposed in the art. Such a molecule would be desirable, as it would leave the major portion of the molecule unchanged and free to bind with the "target" molecule or tissue cells. Additionally, to further enhance tissue targeting specificity, a non-phenyl ring halogenated tamoxifen derivative would preferably be coupled with a "targeting" molecule, such as a microparticle.

Non-phenyl ring halogenated tamoxifen derivatives with enhanced binding affinity, greater specific radioactivity, and which can readily traverse the cell membrane have not as yet been developed in the art. The development of such derivatives would represent a tremendous improvement in the quality of imaging techniques currently available, as well as improve the accuracy of PET and SPECT scans.

Other alternative compounds proposed as possible radiopharmaceuticals useful in the imaging of tissue receptors include labeled progesterone and estrogen derivatives. For example, Pomper et al. described a ligand for the progesterone receptor.[16] The aliphatic fluorination of FENP (21-[$^{18}$F]fluoro-16-$\alpha$-ethyl-19-norprogesterone) is described as demonstrating a high specific uterine target tissue uptake.[16] This ligand for the progesterone receptor was labeled with the positron-emitting radionucleotide fluorine-18 (t $\frac{1}{2}$=110 min).

Estrogen-based imaging agents described in the literature include radionuclides of iodine[20], fluorine[19], and bromine[21]. By way of example, an estrogen-based imaging agent described in the literature is the 16-$\alpha$-[$^{18}$F]fluoro-17-$\beta$-estradiol ligand.[17]

The preparation of 16-$\alpha$-[$^{18}$F]fluoroestrogens and their selective uptake by estrogen target tissues in rats has been described by Kiesewetter et al.[19]. Significant changes in the binding of estrogen receptors in breast tumor were reported with the use of [$^{18}$F]fluoroestradiol using PET.[4] However, the radioisotope $^{18}$F has a very short half life, and therefore techniques and molecules which employ this radioisotope must be rapid, and preferably more rapid than currently employed molecular labeling techniques allow.

Unfortunately, estrogen-based imaging agents are of limited utility in patients receiving estrogen based therapies due to the competition between imaging agents and therapeutic agents for estrogen receptors. Thus, a poor correlation is likely to exist between the actual physiological response within the tumor during hormonal therapy verses the response which is shown by an estrogen-based imaging agent. For these reasons, a progestin-based imaging agent for breast tumors might be preferred over an estrogen-based agent because tumor response to hormonal therapy appears to correlate better with progesterone receptor positivity than with estrogen receptor positivity.[17] It has further been reported that estrogen receptor positive tumors in patients on hormonal therapy (e.g. tamoxifen) could not be imaged with an estrogen, as the circulating levels of tamoxifen and its metabolites are sufficiently high to fully occupy the estrogen receptor[18], making visualization quite difficult.

While the radiolabeled tamoxifen derivatives described in the literature have demonstrated some increase in estrogen receptor binding affinity, they do not demonstrate sufficient specific radioactivity due to the low tamoxifen phenolic ring incorporation of the radioactive halogen atoms. Thus, the derivatives' enhanced affinity for estrogen receptor is offset by a reduction in the radioactivity incorporated.

Moreover, the fluorine ion radioisotope, $^{18}$F, with its reportedly low effective dose equivalency and a short half-life (t $\frac{1}{2}$=110 min) further exacerbates the problem of obtaining sufficiently labeled reagent, which is stable over an experimentally useful period of time.

For these reasons, any method which Would utilize $^{18}$F in labeling the phenyl rings of tamoxifen molecule must be rapid (i.e. within a 2 hour reaction time) to avoid a loss in specific activity of the label.

Currently used tamoxifen derivatives, substituted at the various phenolic sites of the tamoxifen structure, can potentially block the formation of the active metabolite, 4-hydroxytamoxifen. Such a blockage may result in a decrease in receptor binding affinity of the particular tamoxifen analog since the 4-hydoxylated derivative is known to possess higher affinity. Alternatively, a competitive elimination reaction of 4-position substituted analogs may occur in the cytosol through the formation of the active metabolite, 4-hydroxytamoxifen. Such elimination processes are known to sometimes occur after drugs cross cell membranes.

Tamoxifen derivatives which could be more rapidly synthesized, with higher specific radioactivity and/or with improved receptor binding affinity or specificity, would offer a significant advance to the art, especially with regard to the in vivo diagnosis and therapy of estrogen positive tumors and the imaging of estrogen receptors in patients on a hormone-based regimen.

SUMMARY OF THE INVENTION

The present invention provides novel halogenated tamoxifen analogs found to have surprisingly and unexpectedly enhanced binding affinity for estrogen receptors. The particular chemistry of the claimed tamoxifen analogs and derivatives advantageously provides a rapid and simple method for preparing and labeling the tamoxifen molecule at a non-aromatic carbon of tamoxifen, particularly at the aliphatic (alkyl) chain of the native tamoxifen structure demonstrated at Formula 1.

The claimed no-carrier added, aliphatic chain substituted and radiolabeled tamoxifen derivatives are unlike any other labeled tamoxifen derivative described in the literature[13], and possess an enhanced binding affinity for estrogen receptors while retaining high specific radioactivity. Due to this enhanced binding affinity for estrogen receptors, the described tamoxifen derivatives and analogs can be advantageously employed to treat, diagnose and/or monitor estrogen receptor-positive tumors (e.g., hormone dependent cancers). Additionally, the derivatives may also be advantageously used to predict the efficiency of tamoxifen-related therapy of breast tumors.

The term "aliphatic chain" substituted tamoxifen derivative as used in describing the claimed halogen substituted forms of the native tamoxifen molecule refers to chemically substituted forms of the tamoxifen molecule wherein a halogen, haloalkyl or hydroxy group is positioned at other than one of the three phenyl rings of the native tamoxifen structure, and at other than the double carbon bond of the native tamoxifen chemical structure (See Formula 1). Even more particularly, the tamoxifen derivatives of the present invention are defined as including a halogen, haloalkyl or hydroxy group at the end of the aliphatic carbon chain which is pendant to one of the carbons which comprises the double carbon-carbon bond of the native tamoxifen structure.

Any of the family of halogen atoms may be used in conjunction with the claimed invention. By way of example, the halogen atoms include fluorine, bromine, iodine, chlorine and astatine. Those particular halogens most preferred in the present invention include fluorine, bromine, iodine and chlorine.

Applicants' halo-alkyl, halogen and hydroxy substituted tamoxifen derivatives include the halogen atom or hydroxy moiety strategically placed on the aliphatic chain of the tamoxifen molecule. Thus modified, the molecule has greater estrogen receptor binding affinity than native tamoxifen. Additionally, the placement of a halogen atom at the aliphatic side chain, rather than on the aromatic portions of the tamoxifen structure, preserves the major portion of the tamoxifen molecule for binding with estrogen receptors and/or other molecules. Moreover, labeling of the tamoxifen structure at the alkyl site rather than at any of the structures phenolic rings, requires only minimal alteration of the tamoxifen structure. Limited modification of the tamoxifen structure is desirable because phenyl rings and phenoxyethylamine chains are essential for retaining the structure necessary to assure proper conformational fit with extrogen receptors and to facilitate successful entry of the molecule through the cell membrane and into the cytoplasm for in vivo use. As used in the present invention, the term "native" tamoxifen refers to that structure of tamoxifen which is unsubstituted and which corresponds to the chemical structure presented at Formula 1.

The substitution of the N,N-dimethyl group of tamoxifen with an N,N-diethyl group is demonstrated by the inventors to increase estrogen receptor binding with the halogen tamoxifen analog up to 30-fold. The binding affinity of the described halogenated tamoxifen derivatives to estrogen receptors is increased in all cases by at least 4-fold as compared to native tamoxifen.

Radiolabeling of the halogen tamoxifen derivative with [$^{18}$F], [$^{131}$I], [$^{123}$I], [$^{77}$Br] for Spect, or [$^{75}$Br] for PET provides a molecule with both high specific radioactivity and high estrogen receptor binding affinity. Radiolabeled forms of the halogen chloride [Cl] may also be employed In order to account for the short half life of the particular radioisotopes used, the Inventors have optimized the synthesis of these halogenated tamoxifen derivatives to provide relatively high specific radioactivity. These halogenated derivatives are also shown to have high binding affinity for estrogen receptors. The optimization of isotope half life, high estrogen receptor affinity and target cell specificity provides particular advantages for the in vivo imaging of estrogen receptors.

The distinguishing structural features of the claimed aliphatic chain substituted tamoxifen derivatives establish in part the superiority of the claimed analogs over the N,N-dimethyl (phenyl ring substituted) tamoxifen derivatives described by Foster et al. and others.[6] The claimed tamoxifen analogs and derivatives also feature the specific substitution of tamoxifen with a fluorine, iodine, chlorine or bromine halogen atom or lower halo-alkyl group at the aliphatic chain of the tamoxifen molecule, in contrast to the phenyl-ring substituted tamoxifen structure described in Foster et al.[6] The synthesis and chemical structure of the claimed halogenated and halo-alkyl tamoxifen analogs are distinct from all derivatives discussed in the literature, including the phenolic ring-substituted tamoxifen derivative described by McCague in U.S. Pat. No. 4,839,155.

Most generally, the tamoxifen derivatives of the claimed invention comprise the following structure:

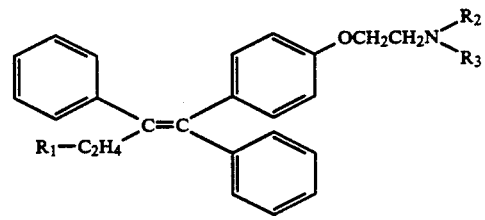

wherein $R_1$ is a halogen or lower halo-alkyl; chloromethyl, bromomethyl-hydroxy, hydroxymethyl, tosyl or tosylmethyl; $R_2$ is a lower alkyl; $R_3$ is a lower alkyl, and wherein $R_2$ is not methyl when $R_3$ is methyl. In a most preferred embodiment of the described tamoxifen derivatives, $R_2$ and $R_3$ are most particularly defined as ethyl. In still another embodiment, $R_2$ is methyl and $R_3$ is ethyl. In particular embodiments of the invention, $R_1$ is fluoromethyl and $R_2$ and $R_3$ are ethyl. In still another embodiment, $R_1$ is iodomethyl and $R_2$ and $R_3$ are ethyl.

A lower halo-alkyl as defined for purposes of the present invention is a carbon chain of less than 5 carbons with a halogen atom attached thereto. A lower alkyl is defined as a carbon chain of less than 5 carbon atoms such as methyl (1-C), ethyl (2-C), propyl (3-C), butyl (4-C) or pentyl (5-C). Most preferably $R_2$ is methyl or ethyl. Similarly, $R_3$ is most preferably methyl or ethyl. However, $R_2$ is not methyl when $R_3$ is methyl.

In a particularly preferred embodiment of the tamoxifen derivatives described herein, $R_1$ is a halogen further defined as bromine, chlorine, fluorine or iodine. Where $R_1$ is a lower halo-alkyl, the lower halo-alkyl by way of example is defined as bromomethyl, fluoromethyl, iodomethyl or chloromethyl. In still a further embodiment of the described tamoxifen derivative, $R_1$ is a lower hydroxy alkyl, such as, for example, hydroxymethyl.

In a second most particularly preferred embodiment, the tamoxifen derivatives included within the scope of the invention are radiolabeled, and comprise:

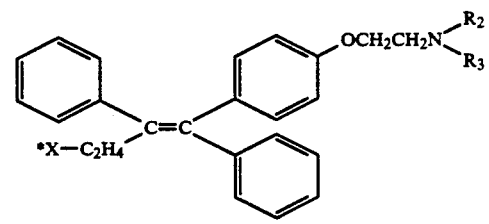

wherein *X is $^{18}$F, $^{131}$I, [$^{18}$F]fluoromethyl, [$^{131}$I]iodomethyl, chloromethyl, or bromomethyl; $R_2$ is methyl or ethyl, and wherein $R_3$ is methyl or ethyl. Most preferably, $R_2$ is not methyl when $R_3$ is methyl. In a particularly preferred embodiment of this particular tamoxifen derivative, *X is [$^{18}$F]fluoromethyl, $R_2$ is ethyl, and $R_3$ is ethyl. The three phenyl rings of the tamoxifen structure are unsubstituted phenyl rings In still another particularly preferred embodiment, *X is [$^{131}$I]iodomethyl, $R_2$ is ethyl and $R_3$ is ethyl.

In still another most preferred embodiment of the claimed tamoxifen derivative, $R_1$ is chloromethyl or chloro, $R_2$ is ethyl and $R_3$ is ethyl. Where bromine is the halogen, $R_1$ is bromomethyl or bromo, $R_2$ is ethyl and $R_3$ is ethyl.

The fluoromethyl tamoxifen derivatives herein disclosed demonstrate an enhanced binding affinity for estrogen receptors compared to other tamoxifen derivatives having a a 30-fold (trans) and 6-fold (cis) enhanced estrogen receptor binding affinity. For iodo-methyl tamoxifen analogs, the trans isomer has a 15-fold and the cis-isomer has a 10-fold enhanced estrogen receptor binding affinity, compared to other tamoxifen derivatives described in the literature. Salituro et al. reported that the cis isomer of tamoxifen azizidine has 50-fold less affinity than the trans isomer. Placing a fluorine atom at the 4-position of phenyl ring has been demonstrated to decrease binding affinity 40-fold when compared to native tamoxifen. Pomper et al describes progestrone analogs only, which have affinity for progesterone receptors. Thus, that data is not directly compared here. (Shani et al.)[38]

The bromomethyl tamoxifen analogs provide for the trans isomer a 50-fold enhancement of estrogen receptor binding affinity, and for the cis isomer, a 38-fold enhancement of estrogen receptor binding affinity. Particular other of the tamoxifen derivatives exhibit at least a 4-fold increase in estrogen receptor binding affinity compared to native tamoxifen.

Because of the enhanced estrogen receptor binding affinity demonstrated by the described tamoxifen derivatives and analogues, Applicants provide an efficient and specific reagent which is useful in the imaging of estrogen receptors. In such an embodiment, the tamoxifen derivative includes a radiolabel "tag", most preferably an $^{18}$F, $^{131}$I, $^{123}$I or $^{75}$Br (for positron) and $^{77}$Br atom (for SPECT). In a most particularly preferred embodiment of the imaging reagent, the "tag" is an $^{18}$F, $^{131}$I, or $^{77}$Br radionucleotide located at the alkyl side chain of the halogen-substituted tamoxifen molecule.

Most preferably, the alkyl side chain (for $R_2$ and $R_3$) comprises a carbon chain of at least two carbons (ethyl). Methods of performing the described radiosynthesis of the disclosed [$^{18}$F]fluoromethyl, [$^{131}$I]iodomethyl, $^{77}$Br bromomethyl tamoxifen derivatives are also provided herein. The radiosynthesis of $^{77}$Br-labeled tamoxifen is similar to the $^{131}$I-labeled analog. Therefore, the methods described herein for the preparation of radiolabeled fluoro and iodo tamoxifen derivatives may be utilized for the preparation of radiolabeled forms of the bromo and chloro derivatives, by using an analogous bromo- or chloro-salt as the starting reagent.

In that the halogenated derivatives of tamoxifen disclosed herein have enhanced estrogen receptor binding affinity, the presently disclosed tamoxifen derivatives provide an improved method by which estrogen receptors may be imaged through a PET or a SPECT radioimaging protocol. Most particularly, the halogen to be used in forming these estrogen binding agents is fluorine, bromine, or iodine.

Additionally, in order to even further enhance the tissue-targeting of the halogen tamoxifen derivatives to those tissues rich in estrogen receptors, the Inventors propose to couple the described radiolabeled, substituted tamoxifen derivatives to microparticles. This coupling can be accomplished by reacting the halogenated tamoxifen with a polymer in the presence of a coupling reagent (e.g., dioyclohexylcarbodiimide) (See FIG. 4). The coupling of the tamoxifen derivative with the microparticle is expected to enhance the molecule targeting to particular tissues. The "payload" (e.g., a chemotherapeutic halogenated tamoxifen derivative) can then be released from microparticles by a diffusion or erosion process and used to kill tumors.

To test this approach, estrone (estrogen agonist) was conjugated to poly(benzyl)glutamate (PBLG). After conjugation, the estrogen receptor binding was determined. The IC$_{50}$ for estrone was $5 \times 10^{-8}$M, whereas the conjugated analog was $5 \times 10^{-7}$M. The conjugation yield was 86% (determined from UV at 282 nm). PBLG polymer loaded with cisplatin (an antitumor agent) showed sustained release properties (particle size 100 $\mu$M). Similar conjugation techniques will be used to conjugate halogenated tamoxifen to PBLG.

Any substituted tamoxifen derivative, wherein the halogen substitution is located at a non-aromatic site of the tamoxifen molecule, specifically at the aliphatic side chain (i.e., the $C_2H_5$ group shown in the native tamoxifen structure), would be capable of functioning as an imaging agent with enhanced estrogen receptor binding affinity. The halogenated tamoxifen derivatives most preferred in the present invention include the bromotamoxifen analogs, such as bromomethyltamoxifen. Of the fluoromethyl derivatives, N-diethylfluoromethyltamoxifen is most preferred. The most preferred iodotamoxifen derivative of the described estrogen receptor radiopharmaceutical agents is iodomethyltamoxifen labeled with $^{131}$I. The most preferred bromotamoxifen derivatives of the present invention include the bromomethyl-tamoxifen analogs labeled with $^{77}$Br.

One object of the present invention is to provide an estrogen receptor imaging reagent which has high affinity for the estrogen receptor and high enough specific activity ($>1$ ci/$\mu$mol) to be suitable for use in positron emission tomography. Another object of the invention is to provide an imaging reagent which, as a result of the foregoing characteristics, has superior target tissue selectivity in vivo. Another object of the present invention is to provide a method for monitoring the effectiveness of tamoxifen therapy in treating breast tumors.

A further object of the present invention is to achieve a substituted tamoxifen derivative which has both high estrogen receptor binding affinity and high specific radioactivity. More specifically, an object of the present invention is to provide an easy and rapid radiosynthesis of substituted tamoxifen derivative (i.e., with fluoro-, iodo-, chloro-, or bromo- or hydroxy-tamoxifen analogs) with high specific radioactivity (e.g., $^{18}$F, $^{131}$I, or $^{77}$Br) at the aliphatic chain of the tamoxifen structure.

By providing a molecular substitution (i.e., halogen, halo alkyl or hydroxy group) at the aliphatic chain of the tamoxifen molecule, the bioactivity of the claimed tamoxifen derivatives is preserved through the retention of the majority of the native structure of the molecule, leaving the majority of the molecule available for binding cell (estrogen) receptors.

An additional object of the invention is to provide a simple and inexpensive method for radiosynthesizing these derivatives.

Methods for preparing the disclosed site specific halogenated tamoxifen derivatives are thus also provided. Currently available methods for directing the substitution of tamoxifen at the aliphatic chain require multiple and time consuming chemical steps. Thus, the formulation of a more efficient and rapid method for preparing halogen alkyl chain substituted tamoxifen derivatives would represent a significant and valuable advance in using particular short half life radiolabeled tamoxifen analogs as radiopharmaceuticals. For example, radionuclide $^{18}F$ analogs have an extremely short half life of only about 2 hours. Therefore, time is of the essence in processing and using $^{18}F$-labeled tamoxifen analog molecules.

An additional object of the present invention is to provide halogenated tamoxifen derivatives which have superior estrogen receptor binding affinities compared to native tamoxifen and to the tamoxifen and progestin derivatives described in the literature.

By way of example, such halogen tamoxifen derivatives of the present invention include fluoro-, iodo-, bromo- and chloro-tamoxifen analogs. In regard to the $IC_{50}$ values, it should be considered that different species (e.g. pig, rat, dog, rabbit) will have different $IC_{50}$ values (for the same compound). However, the Ki should remain the same. Therefore, to report data, one must include a standard sample (e.g., tamoxifen, estradiol, diethylstilbestrol) and compare the relative value to a standard sample. $IC_{50}$ values, therefore, between species cannot be readily compared. Relative binding affinities are more easily comparable. Results of the presently described halogenated alkyl analogs of tamoxifen are therefore expressed in terms of relative binding affinities.

Another object of the present invention is to provide a more stable in vivo reagent. The Inventors nave discovered that one of the advantages of adding halogen atoms to the tamoxifen alkyl chain, instead of at a ring structure of the molecule, is that the molecule has a greater in vivo stability. For example, the active metabolite of tamoxifen is formed at the 4-position of the aromatic ring. If a halogen is placed on the phenyl ring, the halogen-substituted site of the molecule will hinder active metabolite formation. Also, in vivo elimination of halogen may then occur at the phenyl ring to destroy the halogen-substituted forms of tamoxifen. Thus, halogen substitution on the phenyl ring reduces the amount of active metabolite formation in vivo. Substitution of the tamoxifen molecule at the alkyl chain, provides a more stable in vivo reagent as the alkyl chain portion of the tamoxifen molecule does not block the hydroxylation reaction which results in the formation of the active metabolite of tamoxifen.

An additional object of the invention is to provide an effective anti-cancer therapeutic agent for reducing estrogen-receptor positive breast, ovarian, and uterine cancer. The described analogs may also be useful as anti-cancer agents of cancers affecting the estrogen receptor-rich tissue of the brain.

An ultimate object of the present invention is to provide a non-steroid based radiopharmaceutical agent, useful in PET, which has high specific radioactivity and high target tissue selectivity by virtue of its high affinity for the estrogen receptor. The tissue selectivity is capable of further enhancement by coupling this highly selective radiopharmaceutical with targeting agents, such as microparticles.

These objects of the present invention are served with the particular aliphatic substituted tamoxifen derivatives of the present invention. Scratchard analysis of estrogen receptor binding in pig uterus using [H-3]estradiol gave Bmax=376 fmol/mg of protein and Kd=5 nM. The IC-50s ($\mu$M) were: TX,30, FMTX, Cis=5, trans=1; ClMTX, cis=4, trans=0.4; BrMTX, cis=0.8, trans=0.2; ImTX, cis=3, trans=2; OHMTX cis=10, trans=7. For MCF7 breast tumor cell inhibition, the IC-50 of TX was 11 $\mu$M. The relative potencies were TX=100; FMTX, cis=224, trans=93; ClMTX, cis=335, trans=146; BrMTX, cis=2355, trans=298; IMTX, cis=466, trans=175. OHTX, cis=66, trans=50. These results indicate that all of the halogenated analogs of tamoxifen produce greater receptor binding affinity and have more potent tumor cell inhibition than tamoxifen, thus establishing their utility for in vivo imaging of breast tumors.

Additionally, ER binding in pig uterus using [$^3$H] estradiol, Scatchard analysis (N=9) gave Kd=5 nM and Bmax=376 fmol/mg of protein. The Ki (nM) values were: TX=15,000; fluoromethy TX (FMTX), cis=2500, trans=500; iodomethyl—TX (IMTX), cis=1500, trans=1,000. In vivo tissue uptakes in rat (% injected dose per organ, n=5) for $^{131}$I-IMTX (trans) at 3h, 6h, and 24h were: uterus, 0.5±0.04, 0.14±0.16 and 0.01±0.001; liver, 5.3±0.84, 3.0±0.02, 1.7±0.21. Uterus/blood ratios were 1.6, 1.5 and 1.2. The IC50 ($\mu$M) values for MCF7 cell inhibition were TX=11, FMTX, cis=4.5, trans=1.8, IMTX, cis=2.4, trans=6.3 uterus/muscle ratios were 11.0, 7.6 and 3.6.

The following numerical designation of particular tamoxifen compounds is employed throughout the Specification:

Compound I—Tamoxifen
Compound II—N,N-diethyl-hydroxytamoxifen
Compound III—N,N-diethyl-hydroxymethyltamoxifen
Compound IV—N,N-diethyl-fluorotamoxifen
Compound V—Hydroxytamoxifen
Compound VI—N,N-diethyl-fluoromethyltamoxifen
Compound VII—Fluorotamoxifen
Compound VIII—N,N-diethyl-0-tosyltamoxifen
Compound IX—N,N-dimethyl-0-tosylmethyltamoxifen
Compound X—N,N-diethyl-iodomethyltamoxifen
Compound XI—N,N-diethyl-bromomethyltamoxifen
Compound XII—N,N-diethyl-chloromethyltamoxifen The following abbreviations are included throughout the body of the Specification:
BrTX=bromotamoxifen
BrMTX=bromomethyltamoxifen
ClTX=chlorotamoxifen
ClMTX=chloromethyltamoxifen
ITX=iodotamoxifen
IMTX=iodomethyltamoxifen
FTX=fluorotamoxifen (VII)
FMTX=fluoromethyltamoxifen
TX=tamoxifen (I)
$B_{max}$=the total number of binding sites determined from Scatchard analysis.
$E_2$=estradiol
$IC_{50}$=the concentration of test compounds that decreases 50% of specific raioligand binding in receptor assay or 50% of cell viability in MCF-7 cell growth assay.
PET=positron emission tomography
$K_d$ dissociation constant determined from a saturation estrogen receptor assay and a Scatchard analysis.
ER=estrogen receptor FMTX = Fluoromethyltamoxifen
$K_i$ = inhibition constant determined using the equation $$K_i = \frac{IC_{50}}{1 + [^3H] \text{estradiol}/K_d}$$

RBA = relative binding affinity, the relative concentration of estradiol and tamoxifen or its derivatives required to achieve 50% inhibition of [$^3$H]-E$_2$ binding.
RP = relative potency
TX = Tamoxifen

DETAILED DESCRIPTION OF THE PREFERRED EMBODIMENTS

Figure 1:
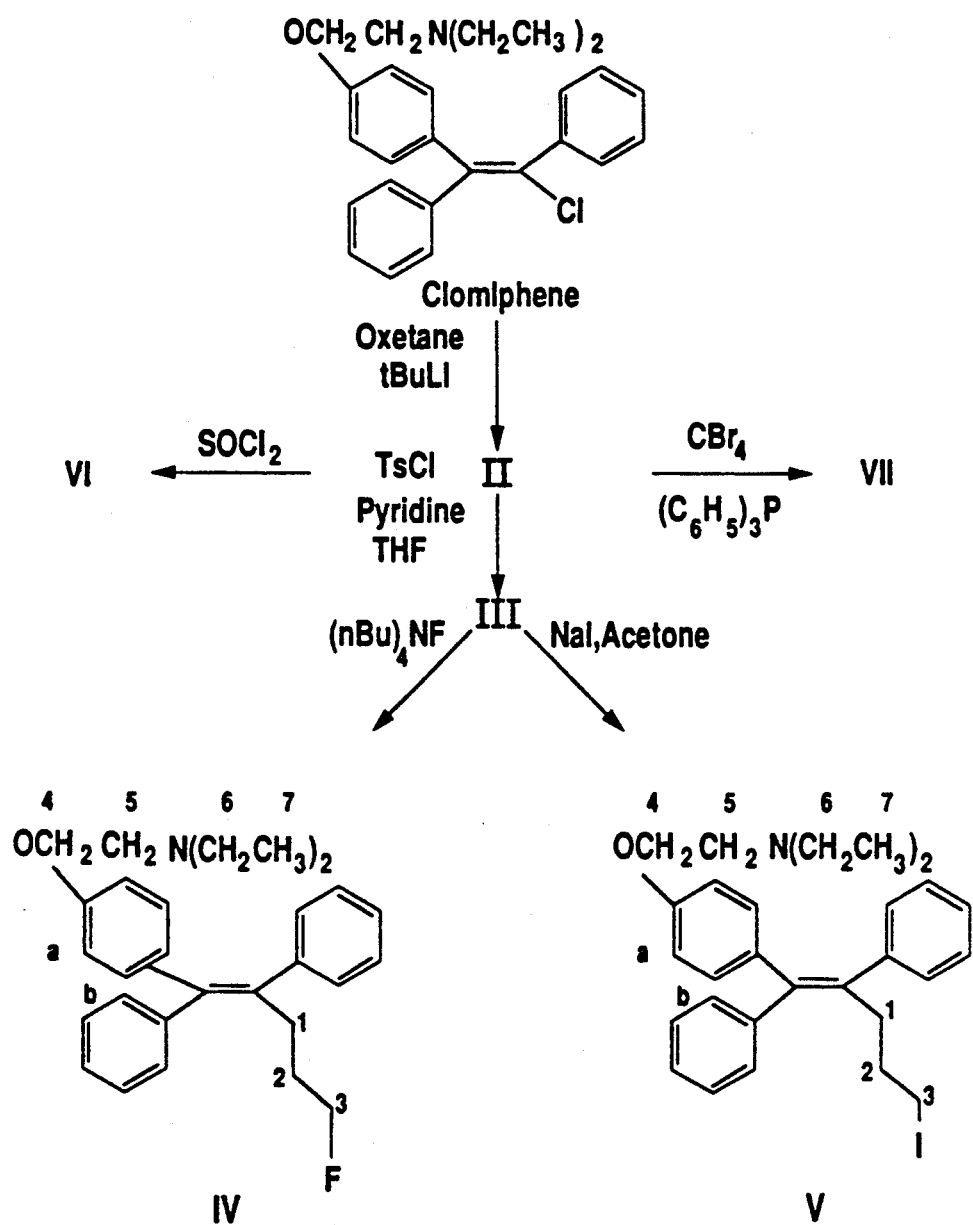
FIG. 1—Synthesis of Tamoxifen Derivatives.

The present invention discloses aliphatic chain-substituted tamoxifen derivatives having markedly enhanced estrogen receptor binding affinity compared to native forms of tamoxifen. The tamoxifen derivatives may include a halogen, a hydroxy or a lower haloalkyl moiety. Any of the halogen molecules Br, Cl, I, or F may be employed in the described site-specific halo and haloalkyl tamoxifen derivatives. Particularly preferred halotamoxifen derivatives of the present invention include fluorotamoxifen (FTX), iodotamoxifen (ITX), bromotamoxifen (BrTX), and chlorotamoxifen (ClTX) iodomethyltaxoxifen (IMTX). By way of example, these lower haloalkyltamoxifen derivatives include clorometyl tamoxifen (ClMTX).

The present invention also includes radiolabeled forms of tamoxifen. The radiolabeled forms of the substituted tamoxifen derivatives provide reagents having high specific activity. These radiolabeled tamoxifen derivatives are demonstrated to be particularly useful in estrogen receptor mapping in estrogen rich tissues, such as the uterus and breast.

Unlabeled forms of the described fluorotamoxifen derivatives were prepared from hydroxytamoxifen via diethylaminosulfur trifluoride reaction at a 47% product yield. The binding affinity of these particularly synthesized fluorotamoxifen derivatives to cytosol estrogen receptors of pig uteri in vitro was higher ($K_i$ is 500 nM; trans-compound VI) than the binding affinity observed between estrogen receptors and native tamoxifen ($K_i$ is 15,000 nM).

Unlabeled forms of iodomethyltamoxifen were prepared from tosyl analogs of tamoxifen by reacting with sodium iodide. The binding affinity of iodotamoxifen was 10–15 fold higher than tamoxifen. The unlabeled forms of chloromethyltamoxifen or bromomethyltamoxifen were prepared by treatment of a tamoxifen hydroxy preecursor with SOCl$_2$ or CBr$_4$, respectively, to provide cloromethyltamoxifen and bromomethyltamoxifen in 87% and 50% yields, respectively.

Radiosynthesis with fluorine-18 was performed on tosyl tamoxifen analogs to produce radiolabeled fluorotamoxifen molecules having the described high specific activity (2–4 Ci/μmol) and a radiochemical yield of 60%. Radiochemical purity was >99%. Radiosynthesis of $^{131}$I-labeled analogs (Compound X) of tamoxifen was performed by reacting tosyl analogs of tamoxifen with NaI. The radiochemical yield was 60%.

The fluoromethyl tamoxifen, cloromethyl tamoxifen, bromomethyl tamoxifen and iodomethyltamoxifen analogs were found to bind to cytosol estrogen receptors of pig uteri and ovaries. IC-50's (μm) for F, Cl, Br, I, and native tamoxifen (TX) were found to be 1, 0.4, 0.2, 2 and 30. These results demonstrate that these halogenated derivatives are effective competitive ligands of [H-3]estradiol (5 nM).

Clomiphene, estradiol, and tamoxifen were obtained from Sigma Chemical Company (St. Louis, Mo.). Flash chromatography according to the procedure of Still et al.[7] was used. Silica gel Sep-Paks from Waters Associates (Milford, Mass.) were used for purifications. Thin-layer chromatographic (TLC) analysis was performed on Whatman K6F silica gel-packed plates (250 μm) (Anspec, Mich.). [$^3$H]estradiol (specific activity 160 Ci/mmol) for receptor binding was purchased from Amersham (Arlington Heights, Ill.). The no-carrier-added Na$^{131}$I was purchased from Syncore. High pressure liquid chromatography (HPLC) was carried out on a LDC system, consisting of two LDC ConstaMetric Pumps, a Rheodyne injector and a Spectra Physics model SP8450 variable UV/Vis detector.

Melting points were determined on a Meltemp melting point apparatus and are uncorrected. $^1$HNMR spectra were obtained from a GE 300 MHz instrument, and mass spectral data were obtained by direct probe analysis (Finnigan MAT INCOS-50) at The University of Texas Health Science Center, Houston, Tex. Elemental analyses were performed by Galbraith Laboratories, Inc., Knoxville, Tenn.

Improved and more efficient methods for the synthesis of all of the described halogenated tamoxifen analogs, including N,N-diethylfluorotamoxifen, fluoromethyl-N,N-diethyltamoxifen, N,N-diethylbromomethyltamoxifen, N,N-diethylchloromethyltamoxifen and iodomethyl-N,N-diethyltamoxifen are also disclosed as part of the invention. For example, the synthesis of fluoromethyltamoxifen and iodotamoxifen (lower alkyl halotamoxifen derivatives) has been simplified from an at least ten (10) step procedure to a more rapid and simple three-step procedure (FIG. 1). The N,N-diethylfluoro (Compound IV) and the N,N-diethylfluoromethyl (Compound VI) and N,N-diethyliodomethyl (Compound X) analogs of tamoxifen were prepared for preliminary evaluation according to these improved protocols. N,N-Diethylfluoro (IV), N,N-diethylfluoromethyl (VI) and N,N-diethyliodomethyl (X)

analogues of tamoxifen were prepared from the corresponding hydroxy analogues of tamoxifen via tosyl analogues by displacement with either sodium fluoride or sodium iodide. N,N-diethylbromomethyltamoxifen (XI) and N,N diethyl-chloromethyltamoxifen (XII) analogs of tamoxifen were prepared from the corresponding hydroxy precursors of tamoxifen with $CBr_4$ or $SOCl_2$, respectively. Mixtures of the cis- and trans-isomers of the respective alkyl-chain substituted tamoxifen derivatives were obtained from this synthesis.

The cis- and trans- isomer products of each of the reactions described above were separated by passing the reaction mixture through a silica gel-packed column and eluting with ether/petroleum ether/triethylamine (1:1:0.1). The $^1$HNMR chemical shift signals for cis- and trans- isomers were assigned based on published information.[8,11]

It was ascertained that the tosyl group on N,N-diethyl-O-tosyltamoxifen could be displaced by nucleophilic fluoride substitution reaction with a milder condition (e.g. kriptofix-222 and KF). Using this procedure, the fluoro-analogue of tamoxifen, compound IV, was prepared in 40% yield from the corresponding tosyl derivative of hydroxytamoxifen. However, elimination occurred to form the butadiene by-product in the presence of the stronger base (e.g. tetrabutylammoniumhydroxide). The formation of the butadiene by-product is due to an elimination reaction on the tosyl analogue.

tamoxifen. The yield for Compound X was 50% (trans) and 70% (cis). Compound X showed a 10-fold (cis) and 15-fold (trans) higher ER affinity than tamoxifen. Receptor binding affinity of fluorotamoxifen, with a fluorine atom placed on the phenyl ring of tamoxifen, and of iodotamoxifen, with an iodine atom placed on the phenyl ring of tamoxifen, has been reported.[22,23] However, that reaction for fluorotamoxifen preparation takes longer and yields lower specific radioactivity for $^{18}F$-labeled tamoxifen, which is not practical for estrogen-receptor studies using PET.

The iodine atom placed on a phenyl ring at the 2-position next to the phenoxy ring gave poor estrogen receptor binding. The iodine atom placed on the 4-position of the aromatic ring gave good receptor binding[13], yet it may be unstable in vivo due to an elimination reaction, resulting in formation of the active hydroxy metabolite. Also, the iodine atom is quite bulky, and may change the planar conformation (e.g., phenyl ring) impairing the binding to estrogen receptors, thereby decreasing binding affinity.

As used in the present invention, the term "lower alkyl" refers to a carbon chain of less than 5 carbon atoms in length. Most preferably the lower alkyl comprises 1 carbon (methyl) or 2 carbons (ethyl).

The following Examples are presented only to describe preferred embodiments and utilities of the present invention, and to satisfy best mode requirements. The

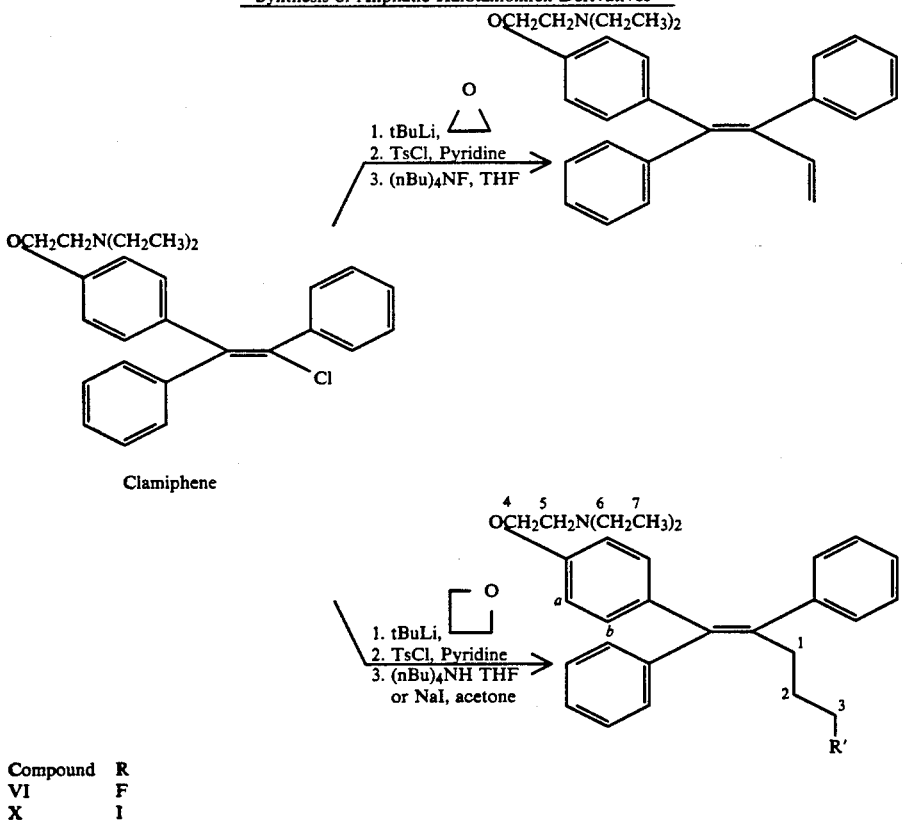

| Compound | R |
|---|---|
| VI | F |
| X | I |

Increasing the side chain by one carbon results in the synthesis of Cis-N,N-diethylfluoromethyltamoxifen (VI), which is more stable toward tosyl elimination. The yield for compound VI was 60%. Compound VI showed a 6-fold (cis) and 30-fold (trans) higher affinity for the estradiol receptor binding site than native examples are not meant to limit the scope of the present invention unless specifically indicated otherwise in the claims appended hereto.

EXAMPLE 1

Synthesis of Trans-Fluorotamoxifen (Compound VII)

Hydroxytamoxifen (trans) (V) (8) (330 mg, 0.85 mmol) was dissolved in methylene chloride (20 ml), cooled to −40° C. and then treated with triethylamine (200 μl) added. Diethylaminosulfur trifluoride (250 μl, 1.89 mmol) was added and the reaction mixture was stirred for 1 hour at −40° C. according to the inventor previous published method.[9] The reaction mixture was then washed with water and the methylene chloride layer evaporated to dryness. The reaction mixture was chromatographed on a silica gel column using 1:1:0.1 hexane/ethylacetate/triethylamine as eluant to yield 145 mg (43.7%) of VII:$R_f$ 0.40 (1:1:0.1 ether/petroleum ether/triethylamine); $^1$HNMR (CDCl$_3$) δ2.29 (S, 6, NMe$_2$) 2.66 (t, J=5.6 Hz, 2, OCH$_2$CH$_2$N), 2.87 (dt, J=21.2 Hz, 6.3 Hz, 2, CH$_2$CH$_2$F), 3.93 (t, J=5.5 Hz, 2, OCH$_2$CH$_2$N), 4.34 (dt, J=47.2 Hz, 6.3 Hz, 2, CH$_2$F), 6.56 (d, J=8.5 Hz, 2, ArH 3,5 to OCH$_2$), 6.77 (d, J=8.3 Hz, 2, ArH 2,6 to OCH$_2$), 7.12-7.35 (m, 10, ArH); m/Z 389 (12, M+), 342 (30, +CH$_2$—CH$_2$—F).

EXAMPLE 2

Synthesis of N,N-Diethylhydroxytamoxifen (Compound II)

Clomiphene (6.06 g, 14.9 mmol) was dissolved in tetrahydrofuran (100 ml) and cooled to −40° C. t-Butyl lithium (1M in pentane, 24 mmol) was added slowly. After 5 minutes, ethylene oxide (14.6 ml, 290 mmol) was added, and the reaction mixture was stirred for 6 hours, poured into water and extracted with ether. The ether layer was evaporated and chromatographed on a silica gel column using 1:1:0.1 ether/petroleum ether/triethylamine as eluant to yield trans product (1.96 g, 27.1%, oil): and cis product (1.56 g, 21.5%, oil): Assignment of $^1$HNMR for aliphatic protons are presented in Table 1.

EXAMPLE 3

Synthesis of N,N-Diethyl-O-Tosyltamoxifen (Compound VIII)

Cis- or trans- N,N-diethylhydroxytamoxifen (II) (100 mg, 0.27 mmol) was dissolved in methylene chloride (2 ml) and cooled to 0° C. Pyridine (150 μl) and tosyl chloride (55 mg, 0.27 mmol) were added. After 2 hours, the reaction mixture was diluted with methylene chloride and washed with water. The methylene chloride layer was evaporated and chromatographed on a $^{18}$C column using 85:15:1 acetonitrile/water/triethylamine as eluant to yield cis (51 mg, 34%, oil) or trans tosyl analog (30 mg, 20%, oil): m/z 569(60, M+), 397(20, +OSO$_2$PhCH$_3$). Values for aliphatic protons are presented in Table 1.

EXAMPLE 4

Synthesis of N,N-Diethylfluorotamoxifen (Compound IV)

The present example is provided to demonstrate two methods by which compound IV may be prepared.

Method 1

Cis or trans N,N-diethylhyroxytamoxifen (II) (400 mg, 0.96 mmol) was dissolved in tetrahydrofuran (25 ml), and the solution was cooled to −40° C. A solution of triethylamine (480 μl) was added. Diethylaminosulfur trifluoride (1280 μl, 2.11 mmol) was added and the reaction mixture was stirred for three hours at −40° C. The crude material was poured into water and then extracted with ether. The ether layer was dried over anhydrous magnesium sulfate, filtered and evaporated to dryness. The mother liquor was chromatographed on a silica gel packed (3×60 cm, ACE Gloss) column using 1:1:0.1 ether/petroleum ether/triethylamine to yield purified 60 mg (15%) of trans IV (oil): Rf 0.70, and 80 mg (20%) of cis IV (oil), Rf 0.60 (1:1:0.1 ether/petroleum ether/triethylamine); trans $^1$HNMR (CDCl$_3$) δ1.02(t, J=7.3 Hz, 6, (CH$_3$CH$_2$N), 2.57 (q, J=7.1 Hz, 4, CH$_3$CH$_2$N), 2.78(t,J=6.3 Hz, 2, OCH$_2$CH$_2$N), 2.91 (dt, J=21.5 Hz, 6.3 H, 2, CH$_2$CH$_2$F), 3.90 (t, J=6.2 Hz, 2, OCH$_2$CH$_2$N), 4.33 (dt, J=47.4 Hz, 6.3 Hz, 2, CH$_2$CH$_2$F), 6.56 (d, J=8.5 Hz, 2, ArH 3,5 to OCH$_2$), 6.75 (d, J=8.7 Hz, 2, ArH 2,6 to OCH$_2$), 7.12-7.37 (m, 10, ArH); m/z 417(50,M+)Hz. Anal. (C$_{28}$H$_{32}$NOF·¼H$_2$O) C, H, N. Calc., C:79.40.H:7.70, N:3, 31; Found, C:79.71, H:7.61, N:3.36.cis $^1$HNMR (CDCl$_3$) δ1.08 (t, J=7.1 Hz, 6, CH$_3$CH$_2$N), 2.64 (q, J=7.3 Hz, 4, CH$_3$CH$_2$N), 2.89-2.96 (m, 4, OCH$_2$CH$_2$N and CH$_2$CH$_2$F), 4.06 (t, J=6.4 Hz, 2 OCH$_2$CH$_2$F), 4.35(dt, J=47.1 Hz, 6.4 Hz, 2, CH$_2$CH$_2$F), 6.89-7.26 (m, 14, ArH); m/z 417 (70, M+), 402 (30). m.p. 55°-57° C. Anal. (C$_{28}$H$_{32}$NOF·0.5 H$_2$O) C,H,M, calc., C:78.84, H:7.80, N:3.28; Found, C:78.71, H:7.48, N:3.20

Method 2

N,N-Diethyl tosyl analogue of tamoxifen (VIII) (40 mg, 0.07 mmol) was dissolved in tetrahydrofuran (200 μl) and then treated with tetrabutylammonium fluoride (170 μl, 1M in tetrahydrofuran). Fifteen minutes after adding TBAF, two spots were visualized by silica gel TLC (4:1 chloroform/methanol). Both products were isolated from a silica gel Sep-Pak by elution with ether/petroleum ether/triethylamine (1:1:0.1). One product isolated was the trans isomer of compound (IV) (11 mg, 40%) and the other was a butadiene derivative (30%, oil). Butadiene derivative $^1$HNMR (CDCl$_3$) δ1.08 (t, J=7.0 Hz, 6, CH$_3$CH$_2$N), 2.65 (q, J=7.0 Hz, 4, CH$_3$CH$_2$N), 2.90 (t, J=6.0 Hz, 2, OCH$_2$CH$_2$N), 4.08 (t, J=6.0 Hz, 2, OCH$_2$CH$_2$N), 4.94 (d, J=17.2 Hz, 1 m CH=CH$_2$), 5.17 (d, J=10.9 Hz, 1, CH=CH$_2$), 6.78-7.26 (m, 9, ArH and CH=CH$_2$). m/z 397 (60, M+). Anal. (C$_{28}$H$_{31}$ NO.1.5 H$_2$O) C,H,N. Calc., C:79.21, H: 8.06: N:3.30; Found, C:79.76, H:7.56, N:3.09.

1,5H$_2$O indicates that the sample is either not dry enough or hydroscopic.

EXAMPLE 5

Synthesis of N,N-Diethylhydroxymethyltamoxifen (Compound III)

Clomiphene (3.8 g, 9.3 mmol) was dissolved in tetrahydrofuran (50 ml), cooled to −40° C. and then treated with t-butyl lithium (1M in pentane, 20 mmol). After 10 minutes, trimethylene oxide (6 ml, 93 mmol) was added, the mixture stirred for 16 hours at room temperature, and then poured into water. The product was extracted with ether and chromatographed on a silica gel column using 1:1:0.1 ether/petroleum ether/triethylamine as eluant to yield purified trans-product (1 g, 25%), m.p. 93°-95° C. and cis product (N,N-diethylhydroxymethyl tamoxifen) (1.0 g, 25%), m.p. 85°-87 ®  C. Anal. (C$_{29}$H$_{35}$ NO$_2$) C,H,N: Calc., C:81.08, H:8.21, N:3.26; Found, C:80.56, H:7.94, N:3.32. Values for aliphatic protons are presented in Table 1.

EXAMPLE 6

Synthesis of Cis-N,N-Diethyl-O-Tosylmethyltamoxifen (Compound IX)

Cis-N,N-diethylhydroxymethyltamoxifen (500 mg, 1.17 mmol) (III) was dissolved in methylene chloride (20 ml), and the solution cooled to 0° C. pyridine (0.66 ml) and tosyl chloride (266 mg, 1.40 mmol) were added. After 4 hours, the reaction mixture was diluted with additional methylene chloride (20 ml) and washed with water, dried over magnesium sulfate, filtered, and evaporated to yield 476 mg. The crude mixture was chromatographed on a $^{18}C$ reverse phase column using 85:15:1 acetonitrile/water/triethylamine as eluant to yield the purified cis tosyl analogue of IX (200 mg, 29%, oil) $R_f$ 0.35 (silica gel plates, ether/petroleum ether/triethylamine 1:1:0.1), m/z 583(10, M+) Values for aliphatic protons are presented in Table 1.

EXAMPLE 7

Synthesis of N,N-Diethylfluoromethyltamoxifen (Compound VI)

The cis- or trans-tosyl analogue of IX (117 mg, 0.2 mmol) was dissolved in tetrahydrofuran (400 μl) according to the inventors' reported procedure.[9] Tetrabutylammonium fluoride (485 μl, 1M in tetrahydrofuran) was added, and the reaction was warmed to 80° C. After 30 minutes, the reaction was completed. The mixture was then hydrolyzed with 6N HCl 6.2 ml for 10 min. The product was chromatographed on a silica gel column, which was eluted with 1:1:0.1 ether/petroleum ether/triethylamine to yield 52 mg (60%, oil) of purified cis fluoro product (VI) or 40 mg (46% oil) of trans product $R_f$0.80 (silica gel plates, ether/petroleum ether/triethylamine 1:1:01), m/z 431(40, M+). Anal. ($C_{29}H_{34}NOF$) C,H,N: Calc., C:80.71, H:7.94, N:3.25; Found, C;80.39, H;8.02, N;3.13 (cis) or C:79.58, H:8.01, N:3.20; $^1HNMR$ AND $^{13}C$—NMR data are shown in Table 2.

EXAMPLE 8

Preparation of N,N-Diethyliodomethyltamoxifen (Compound X)

Tosyl analog of tamoxifen (117 mg. 0.2 mmol) was dissolved in acetone (15 ml). Sodium iodide (150 mg, 1.0 mmol) was added, and the reaction was refluxed for 6h. The mixture was evaporated to dryness and chromatographed on a silica gel column using ether/petroleum ether/triethylamine (1:1:15%) eluant to yield cis 75 mg (70%) $R_f$0.50; or trans 54 mg (50%), $R_f$0.65 (1% triethylamine in ether/petroleum ether; 1:1). m/z 539 (M+, 100), 524(20), 312(30), 191(30), 100(60), 86(100). trans m/z 539 (M+,100), 524(30), 452(20), 312(20), 191(30), 100(60), 86(100). The $^1HNMR$ and $^{13}CNMR$ assignments are shown in Table 3.

The end product N,N-Diethyliodomethyltamoxifen will then be radiolabeled with $^{131}I$, as described in Example 12.

EXAMPLE 9

Synthesis of N,N-Diethylbromomethyltamoxifen (Compound XI)

The present example is provided to demonstrate the most preferred method and best mode for preparing the bromo-tamoxifen analogs of the present invention. Generally, the bromomethyl-tamoxifen analogs were prepared by treatment of hydroxy precursor with $CBr_4$ in 50% yields. The IC-50 with (Br) per (μm) was 0.2. The bromomethyl-Tx analogs were found to bind to estrogen receptors greater than other halogenated tamoxifens tested with F, Cl, or I.

SYNTHESIS

1-[4-(2-Diethylaminoethoxy)phenyl-1,2-diphenyl-5-bromo-1-entene (N,N-Diethylbromomethyltamoxifen)

Triphenylphosphine (105 mg, 0.4 mmol) was added to a stirred solution of hydroymethyltamoxifen (85 mg. 0.2 mmol) (1) and carbon tetrabromide (100 mg, 0 6 mmol) in THF (10 ml). After 2h, the reaction mixture was filtered and the filtrate was evaporated to dryness. The mixture was reconstituted in chloroform (100 μl) and chromatographed on a silica gel column using ether/petroleum ether/triethylamine (1:1:10%) as eluant to yield the cis (36 mg, 37%) or trans (39 mg, 40%) product. Elemental analysis—($C_{29}H_{34}NOBr$) C,H,N: Calc. Trans—C:70.72, H:6.96, N:2.84, Found Trans—C:70.45, H:7.11, N:2.68; Calc. Cis($H_2O$)—C:68.29, H:7.11, N:2.99, Found Cis—C:68.70, H:7.63, N:2.74. Trans—m/z 493 (20mt), 491 (20); Cis—m/z 493 (20, M+), 491(20), 267 (20), 252 (30), 191 (40), 86 (100).

EXAMPLE 10

Synthesis of N,N-Diethylcloromethylamoxifen Compound (XII)

The present example is provided to demonstrate the most preferred method and best mode for preparing the chloro-tamoxifen analogs of the present invention. Generally, the cloromethyl analogs were prepared by treatment of hydroxy precursor with $SOCl_2$ ( 87% yield). The IC-50 (μM) for Cl was 0.4.

SYNTHESIS

1[4-(2-Diethylaminoethoxy)phenyl]-1,2-diphenyl-5-chloro-1-pentene (N,N-Diethylchloromethyltamoxifen)

Thionyl chloride (1 ml) was added to stirred solution of cis or trans hydroxymethyltamoxifen (110 mg, 0.26 mmol) in benzene (25 ml). The mixtures were refluxed for 1 h. Thin-layer chromatography indicated one spot ($R_f$=0.45, Et$_2$O/petroleum ether/triethylamine; 1:1:10%). The reaction mixtures were evaporated and passed through a silica-gel Sep-Pak column eluted with Et$_2$O/petroleum ether/triethylamine (1:1:10%). The cis isomer obtained was 100 mg (87%); the trans isomer was 90 mg (78%). HPLC analysis showed that the retention time for cis isomer was 5.17 min and trans isomer was 5.34 min at flow rate 2 ml/min, U.V.=254 nm, on a C-18 column, mobile phase: acetonitrile:water:triethylamine (85:15:1%); U.V.=254 nm. Elemental analysis—($C_{29}H_{34}NOCl$) C,H,N: Calc. (cis=trans-)—C:77.74, H:7.65, N:3.12, Found Cis—C:77.28, H:7.83, N:3.01; Found Trans—C:77.45, H:7.73, N:2.87. Trans—m/z 450 (20, M+), 448 (60), 447 (100); Cis—m/z 450 (15, M+), 448 (45), 447(50);

TABLE 1

| | Elemental Analysis | | | | | |
|---|---|---|---|---|---|---|
| | Bromide | | | | Chloride | |
| | Calc. | | Found | | Calc. | Found | |
| | | $H_2O$ | Cis($H_2O$) | trans | | Cis | trans |
| C | 70.72 | 68.29 | 68.70 | 70.45 | 77.74 | 77.28 | 77.45 |
| H | 6.96 | 7.11 | 7.63 | 7.11 | 7.65 | 7.83 | 7.73 |
| N | 2.84 | 2.99 | 2.74 | 2.68 | 3.12 | 3.01 | 2.87 |

EXAMPLE 11

$^1$H—NMR and $^{13}$C—NMR Assignment of Fluorotamoxifen Derivatives

$^1$HNMR Assignment

Assignment of $^1$H—NMR for compound VI and X was done by two dimensional NMR which includes COSY, Long Range COSY and HC COSY, Long Range HC COSY (COSY Homonuclear Chemical Shift Correlation). The aromatic portion is subdivided into three isolated spin systems at 200 MHz. In the trans isomer, two spin systems were readily established for aromatic protons a and b (Shanni, 1985; McCague, 1988). For compound VI, a correlation among the H1 methylene protons (resonates at 2.76 ppm for cis and 2.55 ppm for trans), the H2 geminal methylene protons (resonates at 1.79 ppm for cis and 1.80 ppm for trans) and H3 protons (resonates at 4.38 ppm for cis and 4.42 ppm for trans) was observed during the analysis of the COSY Spectrum as shown in Table 4. In addition, the protons at the 4 and 5—ethylene bridge correlated with each other using the COSY spectrum analysis. H-5 resonates down field at 3.99 ppm (cis) and 3.91 ppm (trans) whereas H-4 resonates at 2.8 ppm (cis) and 2.79 ppm (trans). H-6 protons of the ethyl group showed a gradruplet (resonates at 2.57 ppm for cis and 2.57 ppm for trans) which directly correlates with H-7 methyl protons at 1.01 ppm (cis) and 1.03 ppm (trans). The $^1$HNMR data are shown at Table 2.

TABLE 2

$^1$H NMR DATA OF TAMOXIFEN DERIVATIVES
(Carbon number shown at Table 5)

| | H-1 | $J_{1,2}$ | $J_{1,2}$ | H-2 | H-3 | $J_{3,4}$ | $J_{3,4}$ | H-4 |
|---|---|---|---|---|---|---|---|---|
| II (Cis) | 2.79 | 6.3 | 6.3 | 3.96 | 2.70 | 7.1 | 7.1 | 3.49 |
| II (trans) | 2.72 | 6.2 | 6.3 | 3.88 | 2.76 | 7.1 | 7.1 | 3.54 |
| III (Cis) | ~2.48 | — | 6.3 | 3.99 | ~2.64 | — | 7.3 | 1.56 |
| III (trans) | ~2.45 | — | 6.4 | 3.90 | 2.77 | 6.4 | 7.3 | 1.59 |
| VIII (Cis) | 2.91 | 6.3 | 7.1 | 3.94 | 2.84 | 7.1 | 6.3 | 4.07 |
| VIII (trans) | ~2.80 | — | — | ~3.89 | ~2.76 | — | — | ~3.94 |
| IX (Cis) | 2.48 | 6.0 | 6.3 | 3.90 | 2.90 | 6.0 | 7.1 | 1.66 |

$^{13}$C—NMR Assignment

Proton resonance assignments were unequivocally assigned by COSY spectrum. Protonated carbon resonance was assigned from HC-COSY spectrum. The chemical shift for cis and trans isomers of compound VI is shown in Table 3 and for compound X is shown in Table 4.

TABLE 3

$^{13}$C (50 MHz) and $^1$H (200 MHz) NMR ASSIGNMENTS FOR N,N-DIETHYLFLUOROMETHYLTAMOXIFEN (VI) in CDCL$_3$

| Atom | $^1$H (±0.02 ppm) Trans | $^1$H (±0.02 ppm) Cis | No. of protons Trans/Cis | $^1$H (multiplicity) $J_{HH}$ (Hz) Trans | $^1$H (multiplicity) $J_{HH}$ (Hz) Cis | No. of carbons | $^{13}$C (ppm) $J_{HH}$ (Hz) Trans | $^{13}$C (ppm) $J_{HH}$ (Hz) Cis |
|---|---|---|---|---|---|---|---|---|
| Ar | 7.25 | 7.23 | 10H | m | m | 6C | 130–157 | 130–157 |
| | | | | | | 10C | 126–132 | 126–131 |
| a | 6.79 | 7.10 | 2H | d(6.8) | m | 1C | 113.5 | 114.2 |
| b | 6.56 | 7.00 | 2H | d(6.8) | m | 1C | 113.5 | 114.2 |
| 3 | 4.42 | 4.38 | 2H | dt(7.3) (6.1) | dt(47.3) (6.10) | 1C | 85.2 (d;165) | 83.5 (d;165) |
| 5 | 3.91 | 3.99 | 2H | t(6.4) | t(6.37) | 1C | 66.3 | 66.6 |
| 4 | 2.79 | 2.80 | 2H | t(6.4) | t(6.37) | 1C | 51.7 | 51.9 |
| 6 | 2.56 | 2.57 | 4H | m | m | 2C | 47.8 | 47.9 |
| 1 | 2.55 | 2.76 | 2H | m | m | | 31.6 (d;5.5) | 31.5 (d;5.5) |
| 2 | 1.8 | 1.79 | 2H | m | m | 1C | 29.8 (d;44.3) | 29.9 (d;19.5) |
| 7 | 1.03 | 1.01 | 6H | t(7.2) | t(7.2) | 2C | 11.8 | 11.8 |

TABLE 4

$^{13}$C (50 MHz) and $^1$H (200 MHz) NMR ASSIGNMENTS FOR N,N-DIETHYLFLUOROMETHYLTAMOXIFEN (X) in CDCL$_3$

| Atom | $^1$H (±0.02 ppm) Trans | $^1$H (±0.02 ppm) Cis | No. of protons Trans/Cis | $^1$H (multiplicity) $J_{HH}$ (Hz) Trans | $^1$H (multiplicity) $J_{HH}$ (Hz) Cis | No. of carbons | $^{13}$C (ppm) $J_{HH}$ (Hz) Trans | $^{13}$C (ppm) $J_{HH}$ (Hz) Cis |
|---|---|---|---|---|---|---|---|---|
| Ar | 7.40 | 7.20 | 10H | m | m | 6C | 135–157 | 135–157 |
| | | | | | | 10C | 126–131 | 126–131 |
| a | 6.76 | 7.10 | 2H | d(8.8) | m | 1C | 113.37 | 114.3 |
| b | 6.54 | 7.00 | 2H | d(8.8) | m | 1C | 113.37 | 114.3 |
| 5 | 3.90 | 4.06 | 2H | t(6.4) | t(6.4) | 1C | 66.16 | 66.64 |
| 4 | 3.02 | 3.04 | 2H | t(7.1) | t(7.0) | 1C | 51.59 | 51.85 |
| 3 | 2.78 | 2.88 | 2H | t(6.4) | t(6.4) | 1C | 6.38 | 6.19 |
| 6 | 2.50 | 2.70 | 4H | m | m | 2C | 47.77 | 47.89 |
| 1 | 2.50 | 2.70 | 2H | m | m | 1C | 37.05 | 37.06 |
| 2 | 1.86 | 1.86 | 2H | pent (7.4) | pent (7.4) | 1C | 32.92 | 32.92 |

TABLE 4-continued 13C (50 MHz) and 1H (200 MHz) NMR ASSIGNMENTS FOR
N,N-DIETHYLFLUOROMETHYLTAMOXIFEN (X) in CDCL3

| Atom | $^1H$ (±0.02 ppm) Trans | $^1H$ (±0.02 ppm) Cis | No. of protons Trans/Cis | $^1H$ (multiplicity) $J_{HH}$ (Hz) Trans | $^1H$ (multiplicity) $J_{HH}$ (Hz) Cis | No. of carbons | $^{13}C$ (ppm) $J_{HH}$ (Hz) Trans | $^{13}C$ (ppm) $J_{HH}$ (Hz) Cis |
|---|---|---|---|---|---|---|---|---|
| 7 | 1.02 | 1.02 | 6H | t(7.1) | t(7.1) | 2C | 11.77 | 11.95 |

EXAMPLE 12

Radiosynthesis of [$^{18}$F] Fluoromethyltamoxifen and [$^{131}$I]Iodomethyltamoxifen from Fluoromethyl Tamoxifen and Iodomethyl Tamoxifen

[$^{18}$F]Fluoride was produced at the University of Texas Health Science Center, Cyclotron Facility, y proton irradiation of [$^{18}$O]water (99.4% isotopic enrichment, ISOTEC INC., Miamisburg, Ohio) in a small volume silver target. Aliquots containing 50-60 mCi of $^{18}$F were combined with kryptofix 222 (26 mg) and potassium carbonate (4.6 mg) and dried acetonitrile. The remaining kryptofix/[$^{18}$F]fluoride was resolubilized in acetonitrile (3 ml).

[$^{18}$F] FLUOROMETHYLTAMOXIFEN

In a typical procedure, potassium [$^{18}$F]fluoride (from azotropic evaporation of $^{18}$F (H$_2$$^{18}$O) in acetonitril in the presence of K$_2$ (03 and Kryptofix 2,2,2) (3 mCi, 200 μl) was transferred to a reaction vessel with the tosylmethyl analog of tamoxifen (compound IX N,N-dimethl-O-tosylmethyltamoxifen) (1 mg). Tosylmethyl analog was prepared essentially as described in Example 6. The vessel was sealed and warmed at 100° C. for 20 minutes, treated with 6N HCl (200 μl), heated for an additional 10 min, and then spotted on a silica gel coated TLC plate for separation (ether/petroleum ether/triethylamine; 1/1/10% or chloroform/methanol; 9/1).

Authentic non-labeled fluorotamoxifen was used to confirm the presence of F-18 labeled compound. The TLC plate was cut into 0.5 cm zones for counting the activity. Using a Davidson multichannel analyzer fitted with a well type NaI crystal with appropriate shielding. The radiochemical yield was determined as 60%. The reaction mixture was passed through a silica Sep-Pak eluted with 10% triethylamine in ether/petroleum ether (1/1). The radiochemical purity was examined using HPLC (C-18 Radial-Pak column, 8×100 mm, 1% triethylamine in acetonitrile/water [85/15], flowrate of 1.5 ml/min). The retention time of compound VI (N,N-diethylfluoromethyltamoxifen) was 5.60 min. Radiochemical purity was >99%. A typical batch had a specific activity of approximately 4–6 Ci/μmol.

[$^{131}$I] IODOMETHYLTAMOXIFEN

For a typical $^{131}$I displacement experiment, Na$^{131}$I (1 mCi) was added to a vial containing tosylmethyltamoxifen (IX)(2 mg) in acetone. The reaction was heated at 100° C. for 30 min. and 6N HCl was added. After 20 minutes, the vial was cooled and the reaction mixture was chromatographed on a silica-gel Sep-Pak column eluted with 1% triethylamine in ether:petroleum ether (1:1). The purity of the [$^{131}$-I] labeled tamoxifen analog was assessed by HPLC and compared to authentic compound. The HPLC retention time for Compound X was 22 minutes (Acetonitrile:water:triethylamine [85:15:1]).

EXAMPLE 13

In Vitro Estrogen Receptor Binding—Various Tamoxifen Derivatives

The present example demonstrates the ability of the described fluorotamoxifen and iodotamoxifen derivatives to bind estrogen receptors in vitro and to demonstrate the utility of employing these tamoxifen derivatives in vivo in various diagnostic and therapeutic applications involving imaging of estrogen receptor-containing tissues.

The relative binding affinity of the tamoxifen derivatives synthesized in Examples 1–8 and of native tamoxifen (Compound I) to estrogen receptor was determined. A previously reported procedure was modified by the Inventors and used for this purpose.[10,11] TEA buffer was used by the Inventors for tissue preparation.

Briefly, uteri (90 gm) were obtained from immature domestic swine (15 kg) was homogenized in Tris buffer (10 mM, pH 7.4) (1 uterus/180 ml), which contained EDTA (1.5 mM) and sodium Azide (3 mM). The homogenate was centrifuged at 100,000 g for 1 hour at 4° C. Uteri cytosol (contains 2% of protein from corresponding uterus tissue) were then pretreated with dextran-coated charcoal as described.[10] Protein concentrations were determined according to the method of Lowry et al.[12]

Figure 2:
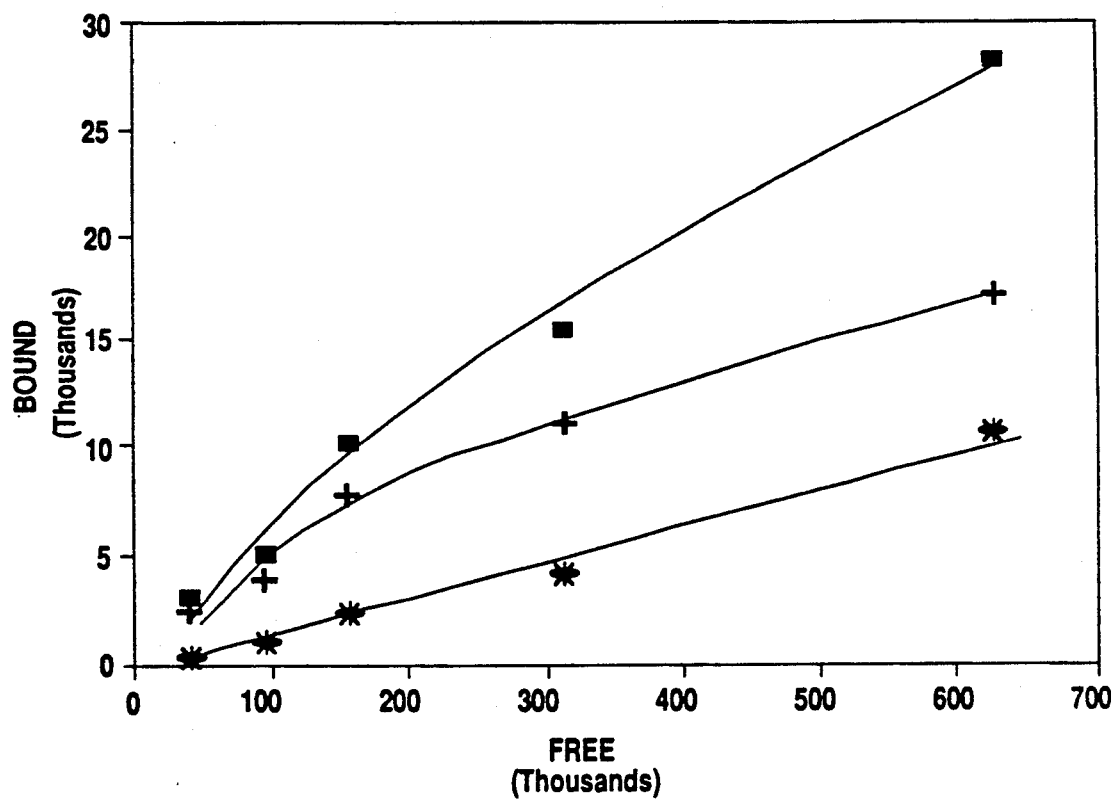
FIG. 2—Estrogen receptor saturation experiment measuring findings in pig uterus in vitro. This is to determine the nature of estradiol interaction with the estrogen receptor site.

To investigate the nature of the interaction of estradiol with the estrogen receptor site, a saturation curve (FIG. 2) was obtained for [$^3$H]estradiol (10$^{-5}$M to 10$^{-10}$M) in the presence or absence of excess estradiol (2×10$^{-5}$M). Uteri cytosol (2 mg protein/tube) were incubated at 4° C. for 2 h with [$^3$H]estradiol (5 nM/tube) and competitor [ranging from 10$^{-4}$M to 10$^{-8}$M ("specific") or with 10$^{-5}$M estradiol (nonspecific)].

Figure 3:
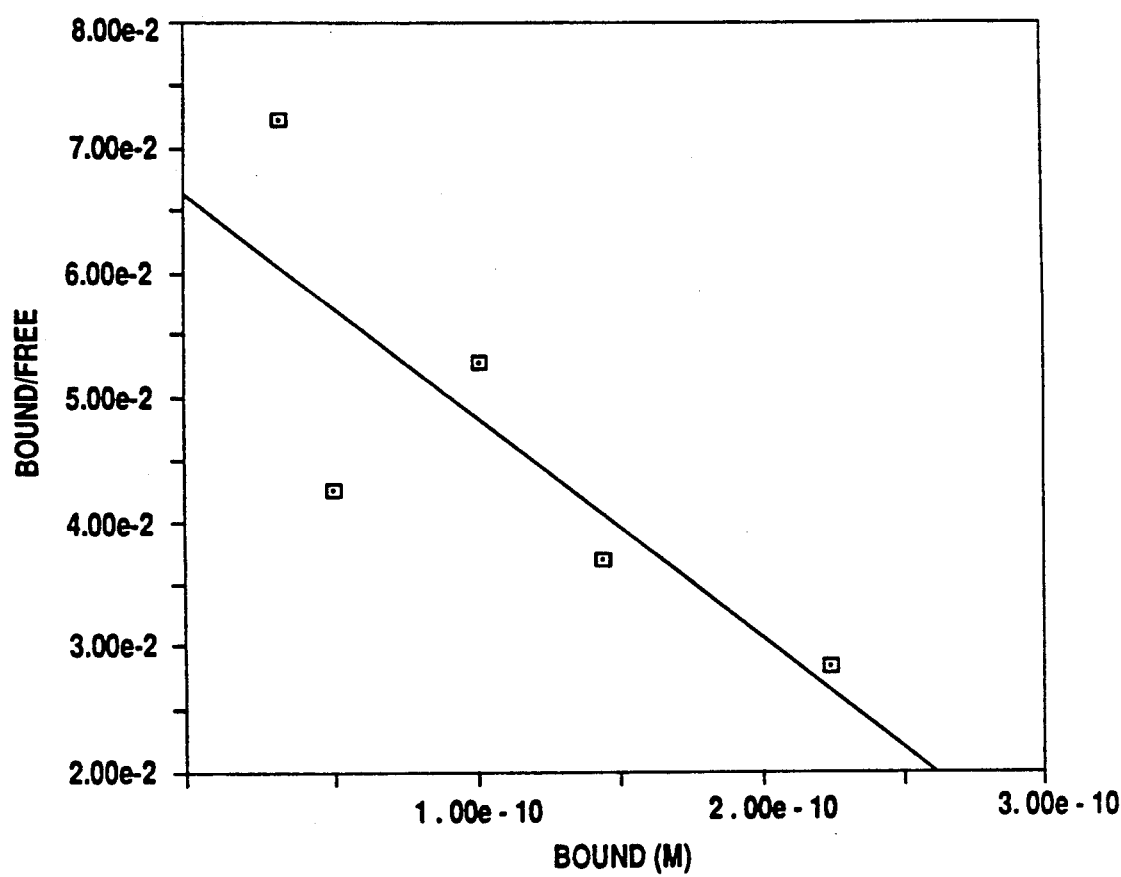
FIG. 3—Estrogen receptor Scatchard plot analysis. This is to demonstrate that estradiol has competitive reversible binding. The receptor density of pig uterus and affinity constant (Kd) were determined.
Figure 4:
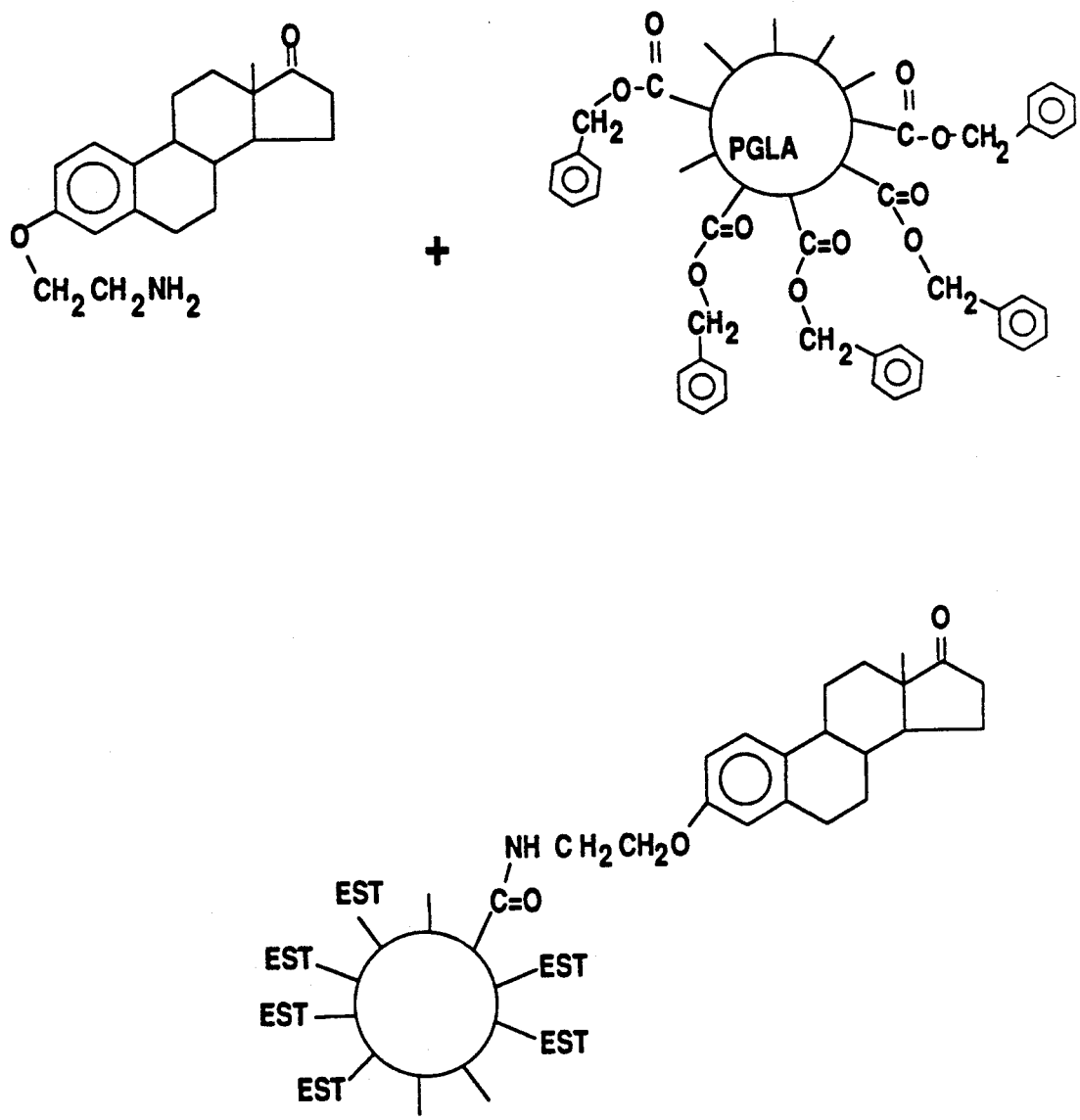
FIG. 4—Diagram of the coupling reaction between estrone (or tamoxifen) and polyglutamate (PGLA).
Figure 5:
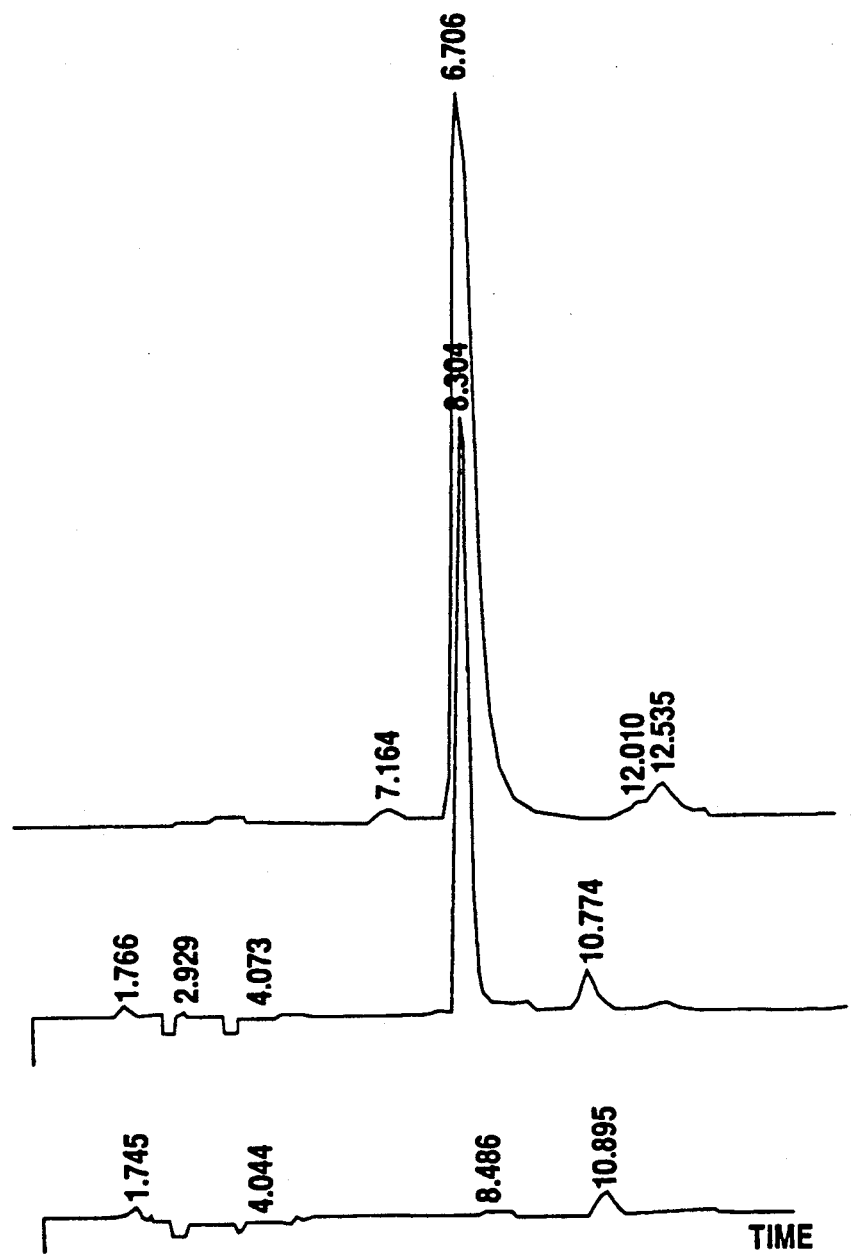
FIG. 5—HPLC Chromatogram of (trans) fluorotamoxifen.
Figure 6:
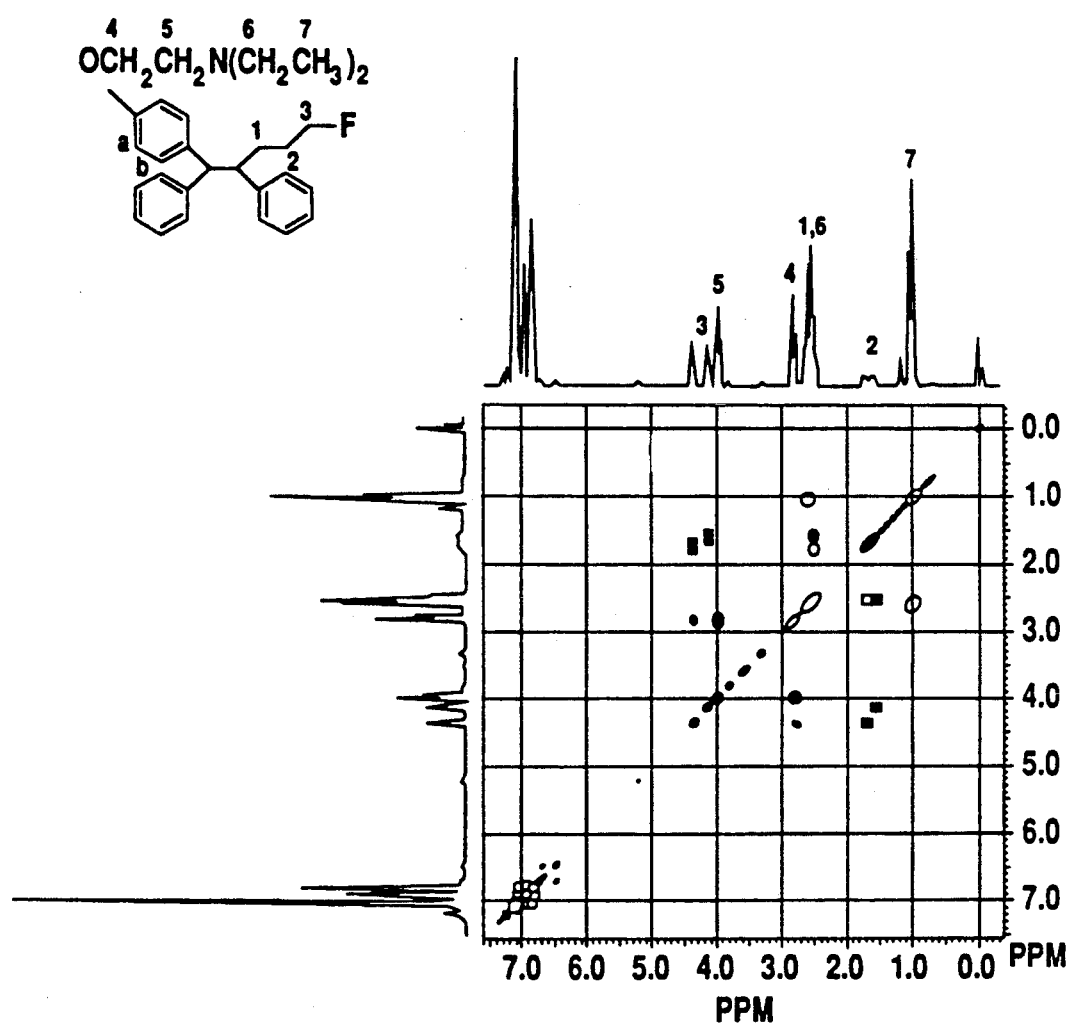
FIG. 6—(cis) fluorotamoxifen Scatchard plot analysis.
Figure 7:
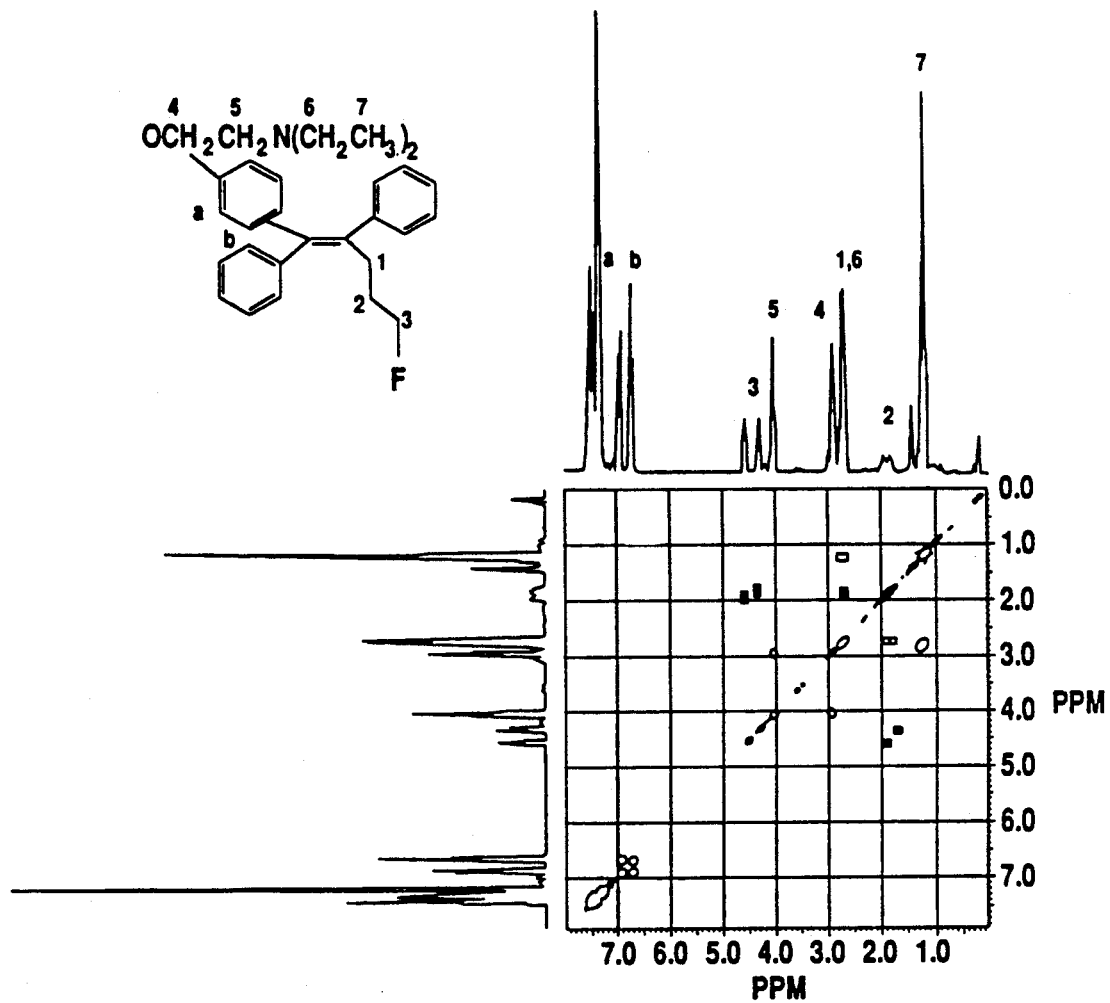
FIG. 7—(trans) fluorotamoxifen Scatchard plot analysis. Notice the presence of the ab "quartet". This quartet is only found in the trans isomer.
Figure 8:
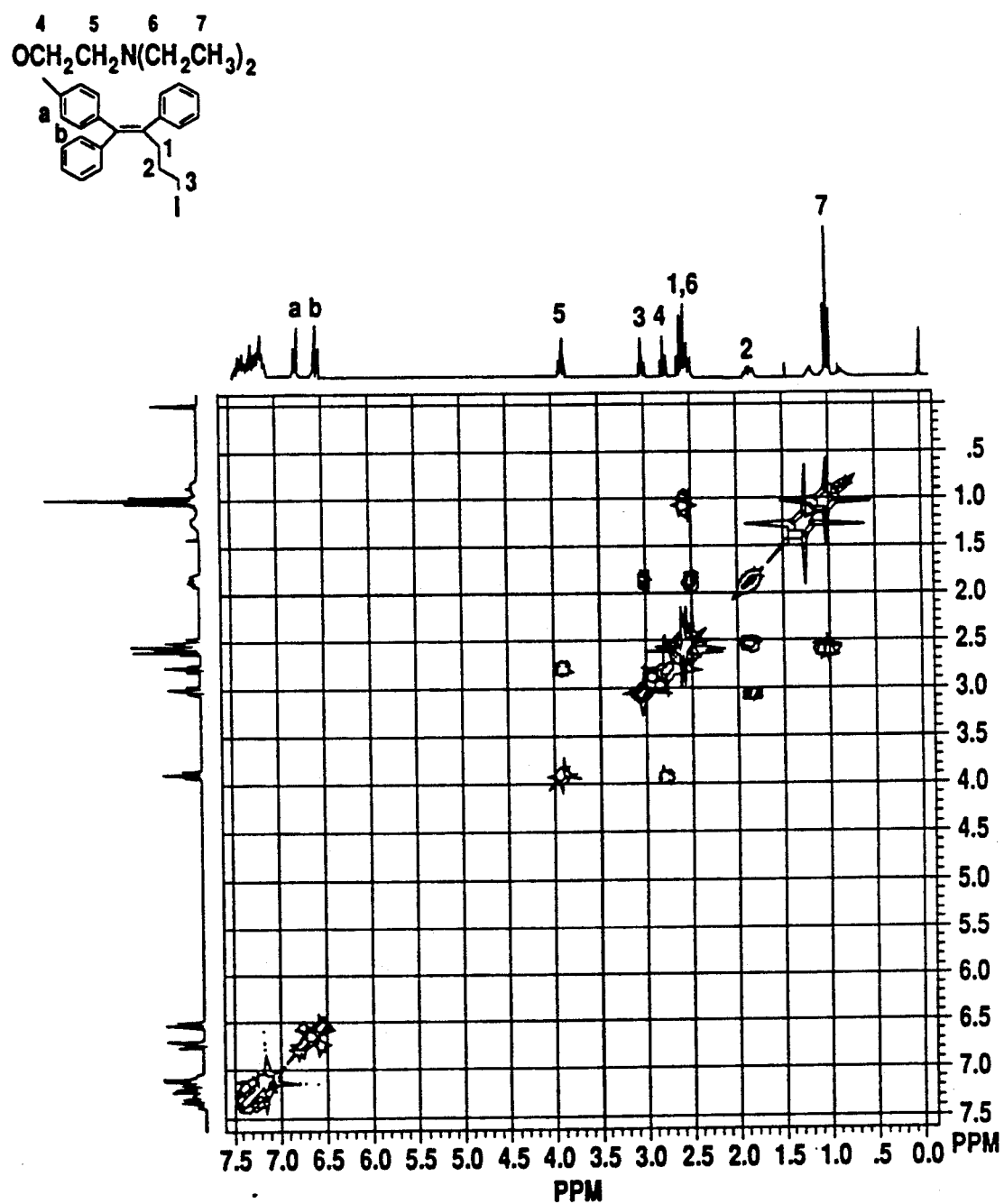
FIG. 8—(trans) iodotamoxifen Scatchard plot analysis. Notice the presence of ab "quartet".
Figure 9:
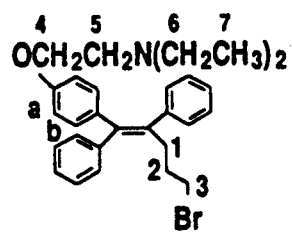
FIG. 9—(trans) bromotamoxifen. Scatchard plot analysis. Notice the presence of the ab "quartet".
Figure 9:
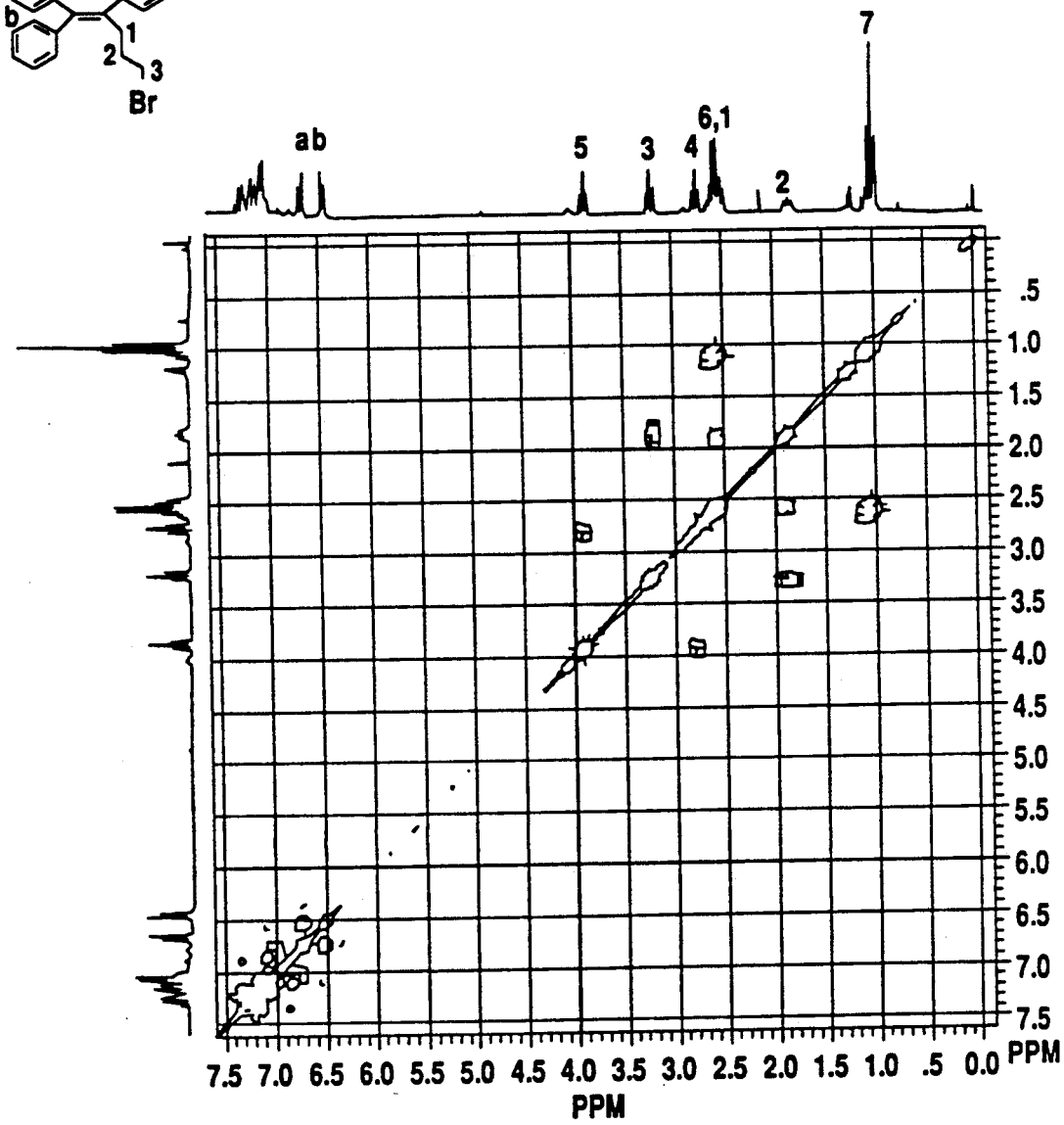
Figure 10:
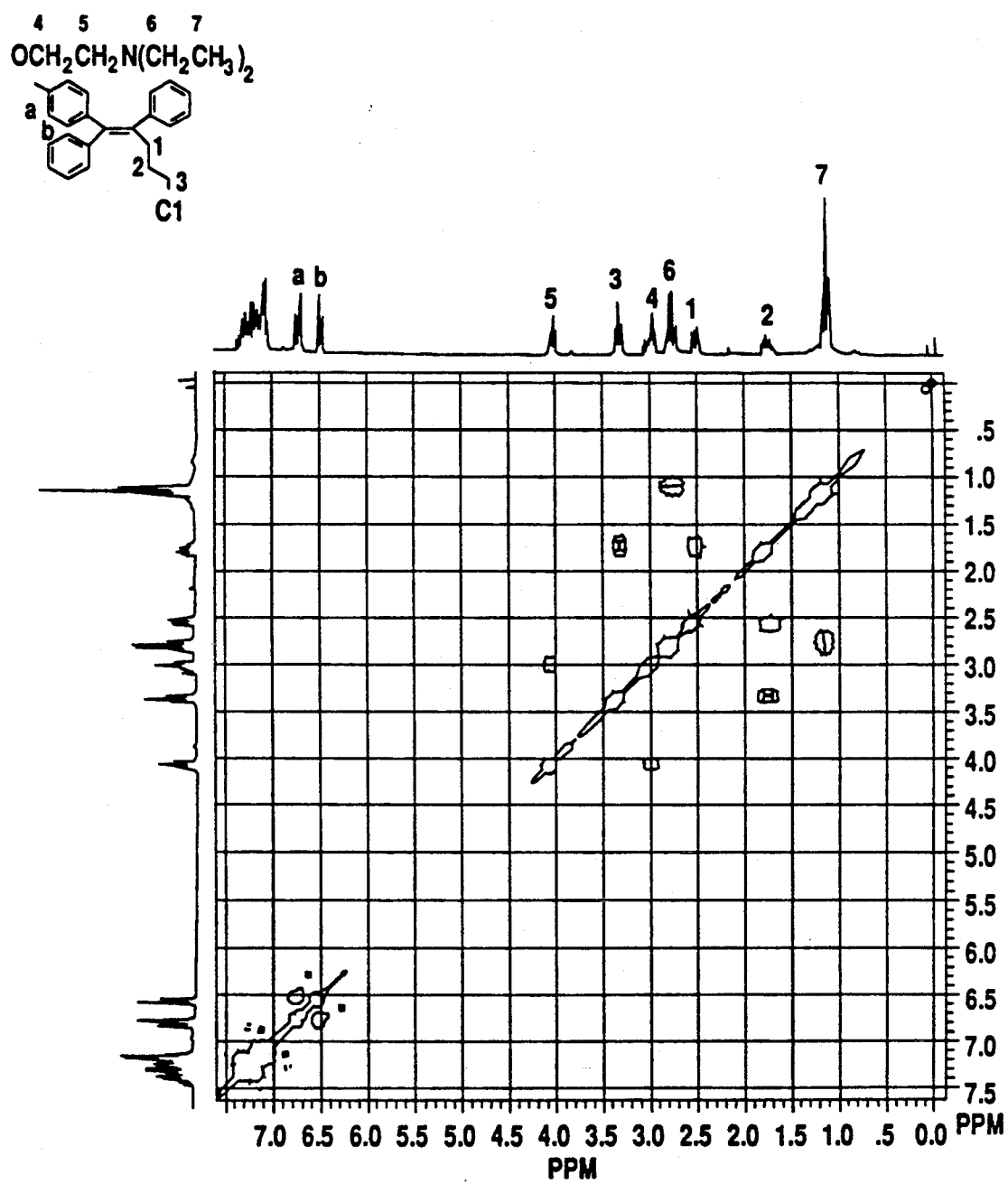
FIG. 10—(trans) bromotamoxifen. Scatchard plot analysis. Notice the presence of the ab "quartet".

A Scatchard analysis indicated a single class of binding sites with a mean K$_d$ of 5 nM (n=9) and a mean B$_{max}$ of 376 fmol/mg protein with a Hill coefficient of 0.982 (FIG. 3).

Various tamoxifen derivatives were then tested for their ability to displace the [$^3$H]estradiol (5 nM) bound to estrogen receptors in this in vitro pig uterus system. From these studies, the concentration of test compounds which decreased 50% of specific radioligand binding (IC$_{50}$) and the inhibition constant (K$_i$) were determined[9] for various tamoxifen derivatives and the results summarized in Table 4.

Tamoxifen (I) (i.e., the fluorotamoxifen derivative) binds to the estrogen receptor with high affinity as tamoxifen (K$_i$=15,000 nM) (Table I). The affinity of the trans isomer of N,N-diethylfluorotamoxifen (IV) for the estrogen receptor is two and a half times that of tamoxifen. In addition, the trans isomer has a higher binding affinity than the cis isomer. Increasing the side chain by one carbon resulted in the formation of fluorinated compound VI, which showed a 6-fold (cis) and 30-fold (trans) higher affinity for the estradiol binding site than tamoxifen. The iodinated compound (X) showed 10-15 fold higher estrogen receptor affinity than native tamoxifen.

TABLE 5
STRUCTURES AND RELATIVE BINDING AFFINITIES OF TAMOXIFEN DERIVATIVES positions 1, 2 on OCH$_2$CH$_2$N(R)$_2$ group; positions 3, 4 on X* group

| Compound | R | X | RBA* | IC$_{50}$ (M) | K$_i$(nM) |
|---|---|---|---|---|---|
| I (Tamoxifen) | CH$_3$ | H | 100 | 3 × 10$^{-5}$ | 15,000 |
| II | C$_2$H$_5$ | OH | | | |
| III (Cis) | C$_2$H$_5$ | CH$_2$OH | 300 | 1 × 10$^{-5}$ | 5,000 |
| (trans) | | | 400 | 7 × 10$^{-6}$ | 3,500 |
| IV (Cis) | C$_2$H$_5$ | F | 100 | 3 × 10$^{-5}$ | 15,000 |
| (trans) | | | 250 | 1.2 × 10$^{-5}$ | 6,000 |
| V | CH$_3$ | OH | | | |
| VI (Cis) | C$_2$H$_5$ | CH$_2$F | 600 | 5 × 10$^{-6}$ | 2,500 |
| (trans) | C$_2$H$_5$ | CH$_2$F | 3,000 | 1 × 10$^{-6}$ | 500 |
| VII (trans) | CH$_3$ | F | 100 | 3 × 10$^{-5}$ | 15,000 |
| VIII | C$_2$H$_5$ | O-tosyl | — | — | — |
| IX | C$_2$H$_5$ | CH$_2$O-tosyl | | | |
| X (cis) | C$_2$H$_5$ | CH$_2$I | 1,000 | 3 × 10$^{-6}$ | 1,500 |
| (trans) | | | 1,500 | 2 × 10$^{-6}$ | 1,000 |
| Estradiol | | | 15,000 | 2 × 10$^{-7}$ | 100 |

*The relative binding affinity (RBA) for the pig uteri estrogen receptor is the ratio between the concentration of unlabeled tamoxifen and the competitor (× 100) (i.e., tamoxifen is 100 as the standard) required to decrease the amount of bound [$^3$H]estradiol by 50%. Incubation was done at 4° C. The data was reproduced in triplicate. The protein concentration was determined to be 1 mg per tube.

EXAMPLE 14

In Vitro Estrogen Receptor Binding—Comparison of Halogenated Tamoxifen Derivatives The present example is presented to demonstrate the estrogen binding activity of various halogenated tamoxifen analogs. The particular halogenated tamoxifen analogs employed in the present study include:
chloromethyltamoxifen (CMTX);
bromomethyltamoxifen (BrMTX);
fluoromethyltamoxifen (FMTX);
iodomethyltamoxifen (IMTX)

The estrogen receptor binding assay used in the present example was essentially the same on described in Example 13.

Non-radiochemical forms of the fluoromethyltamoxifen and the iodomethyltamoxifen were prepared by reacting tosylmethyltamoxifen with KF/kryptofix or NaI resulting in 65% and 47% yields, respectively. The radiochemical yields for [$^{18}$F]FMTX and [$^{131}$I]IMTX were 48% and 40%.

The chloromethyltamoxifen and bromomethyltamoxifen analogs were prepared by treatment of hydroxytamoxifen precursor with SOCl$_2$ or CBr$_4$ resulting in 87% and 50% yields, respectively.

The IC$_{50}$'s for fluoromethyl, chloromethyl, bromomethyl and iodomethyl (F, Cl, Br, I and TX) were 1, 0.4, 0.2, 2 and 30 μM, respectively. These data demonstrate that halogenated tamoxifen analogs, as described herein, compete with [$^3$H]estradiol (5 nM) in binding estrogen receptors.

Bromomethyl tamoxifen, as demonstrated in Table 6, binds to estrogen receptors with greater affinity than the other halogenated tamoxifen analogs tested. These alkyl halogenated tamoxifen analogs, particularly the bromo analogs, are thus expected to be particularly efficacious in the mapping estrogen receptors.

TABLE 6
EFFECT OF HALO ALKYL (METHYLATED) TAMOXIFEN ANALOGS ON ESTROGEN RECEPTOR BINDING[1]

| Compound | IC$_{50}$ (uM)[2] | RBA[3] |
|---|---|---|
| F trans | 1 | 30 |
| Cis | 5 | 6 |
| Cl trans | 0.4 | 75 |
| Cis | 4 | 7.5 |
| Br trans | 0.2 | 150 |
| Cis | 0.8 | 37.5 |
| I trans | 2 | 15 |
| Cis | 3 | 10 |
| Tamoxifen trans | 30 | 1 |
| OH trans | 7 | 4 |
| Cis | 10 | 3 |

[1]Each value shown for IC$_{50}$ and RBA represents the average of three experiments. In each experiment, triplicate samples were tested.
[2]IC$_{50}$: Concentration required to decrease the amount of bound [$^3$H]estradiol by 50%.
[3]RBA: Relative binding affinity is the IC$_{50}$ ratio between tamoxifen and competitor (× 100).

EXAMPLE 15

Inhibition of Breast Tumor Cell Growth In Vitro by Halogenated Tamoxifen Analogs The present example demonstrates the in vitro effect of fluoro, cloro, bromo and iodo-alkyl halogenated tamoxifen analogs on human breast tumor cell growth. This in vitro test demonstrates also the utility of these halogenated tamoxifen analogs for the in vivo treatment of estrogen-dependent cancers, such as human breast and uterine cancers. An additional object of this example was to establish the utility of using the described radiolabeled, alkyl halogenated tamoxifen derivatives as imaging agents for imaging estrogen receptor positive tumors in vivo and to demonstrate the applicability of using the described alkyl halogenated tamoxifen analogs as anti-cancer agents in vivo. It is anticipated that the presently described halogenated tamoxifen analogs will be useful in the treatment of estrogen-dependent breast and uterine cancers, as well as other estrogen-dependent cancer cell growths.

The aliphatically halogenated tamoxifen derivatives described herein (FIG. 1 and Examples 1-12) were used together with an in vitro breast tumor cell system to identify which of these agents might offer advantages over other agents currently in use for the treatment and diagnosis of estrogen receptive tumors.

The MCF7 cell line is a human tumor cell line. This cell line was cultured in MEM (Eagles) media in a 5% CO$^2$ atmosphere with 10% fetal calf serum that had been washed twice with dextran coated charcoal to reduce endogenous estrogen levels. The media was supplemented with 1 mM sodium pyruvate and 100 μm non-essential amino acids. The cell line was screened routinely for myoplasma contamination using the Gen-Probe kit (Fisher). Cells were trypsinized and plated at a density of 5,000 cells/well in 96 well microtiter plates and allowed to attach and recover for 24 hours.

The media was removed by aspiration and replaced with filter sterilized drug (concentration from 10$^{-4}$M to 10$^{-5}$M) in media. The cells were incubated for 72 hours and then stained using the mTT tetrazolium dye assay of Mosmann[36] except that after the media was removed, the blue formazan product was solubilized in 50 μl/well DMSO. Plates were shaken for 1 minute and read on a Dynatech MR600 microplate reader within an hour at a transmission wavelength of 570 nm and reference wavelength of 630 nm.

Compound III (N,N-diethylhydroxymethyltamoxifen), IV (N,N-diethylfluorotamoxifen), VI (N,N-diethylfluoromehtyltamoxifen), VII (fluorotamoxifen), X (N,N-diethyliodomethyltamoxifen), XI (N,N-diethylbromomethyltamoxifen), and XII (N,N-diethylchloromethyltamoxifen) were prepared substantially as described in Examples 1–10.

The results of the 72 hour exposure of MCF7 tumor cell line to tamoxifen or analogs are summarized in Table 6. cis N,N-diethylfluoromethyltamoxifen was 3-fold more potent than tamoxifen control against this tumor cell line. In addition, both cis N,N-diethyl-fluoro, fluoromethyl- and iodomethyl isomers appear to be more potent than the trans isomers.

These results demonstrate that the described fluorotamoxifen derivatives, particularly compounds IV (cis), VI (cis and trans) and X (cis and trans) are effective for inhibiting a breast tumor cell line, and further support the reasonable expectation that these highly specific derivatives would be effective as an anti-cancer agent in treating human breast cancer.

In summary, this study demonstrates that halogenated tamoxifens with the halogen atom placed on the aliphatic chain bind to estrogen receptors in vitro and can be labeled with $^{18}F$ and $^{131}I$, thus reflecting a utility for imaging estrogen receptors by PET and SPECT. Also, the data obtained from in vitro receptor assays suggested that the enclosed tamoxifen derivatives, particularly N,N-diethylfluoromethyltamoxifen and N,N-diethyliodomethyltamoxifen, may be potential ligands for mapping the estrogen receptor by PET and SPECT.

TABLE 7

EFFECT OF HALOGENATED TAMOXIFEN ANALOGS ON HUMAN BREAST TUMOR CELL GROWTH IN VITRO[1]

| Compound | | | $IC_{50}$ Dose (μM)[2] | RP[3] |
|---|---|---|---|---|
| trans-tamoxifen (control) | | | 1.0 (14.6) | 100 |
| (III) | OH | (Cis) | 16.7 | 66 |
| | | (trans) | 22.0 | 50 |
| (IV) | F | (Cis) | 4.1 | 268 |
| | | (trans) | 13.4 | 82 |
| (VI) | FM | (Cis) | 4.5 | 244 |
| | | (trans) | 11.8 | 93 |
| (VII) | FTX | (Cis) | 4.5 | 224 |
| | | (trans) | 11.8 | 93 |

TABLE 7-continued

EFFECT OF HALOGENATED TAMOXIFEN ANALOGS ON HUMAN BREAST TUMOR CELL GROWTH IN VITRO[1]

| Compound | | | $IC_{50}$ Dose (μM)[2] | RP[3] |
|---|---|---|---|---|
| (X) | IM | (Cis) | 2.36 | 466 |
| | | (trans) | 6.3 | 175 |
| (XI) | BrM | (Cis) | 0.62 | 2355 |
| | | (trans) | 4.9 | 298 |
| (XII) | ClM | (Cis) | 4.36 | 335 |
| | | (trans) | 10.0 | 146 |

[1]Cell line used was MCF7. Data represents average of three experiments.
[2]$IC_{50}$ indicates the concentrations required to inhibit 50% of MCF7 cells growth.
[3]Relative potency (RP) indicates the $IC_{50}$ ratio between tamoxifen and competitor.

EXAMPLE 16

In Vivo Biodistribution in Rats of Administered N,N-Diethyl-[$^{18}F$]Fluoromethyltamoxifen (VI)

The present example is presented to demonstrate the particular biodistribution characteristics of an alkyl halogenated tamoxifen derivative administered in an in vivo system.

Four groups of rats (150–200 gm, N=4/group) were anesthetized with ketamine (10–15 mg/rat). Pure N,N-diethyl-$^{18}F$[F]fluoromethyltamoxifen (specific activity >6 Ci/μmol) was reconstructed in 5% ethanol-saline solution, and 10 μC of this tracer was given (i.v., tail-vein) into estrogen-primed female Sprague-Dawley rats ("primed"=60 μg estradiol, s.c., 3 days). Tissue uptake of $^{18}F$-tracer was determined at 2 and 4 hours (h). To ascertain whether the $^{18}F$-tracer uptake was mediated by a receptor-process, one group of rats was given $^{18}F$-tracer without priming with estradiol; and another group of rats was given unlabeled estradiol (30 μg/rat) together with $^{18}F$-tracer. The amount of unlabeled estradiol given to rats should occupy estrogen receptors and chase out the $^{18}F$-tracer's radioactivity from uterus.

TABLE 8

BIODISTRIBUTION OF N,N-DIETHYL-[$^{18}F$]FLUOROMETHYLTAMOXIFEN % OF INJECTED DOSE/GRAM OF TISSUE WEIGHT OF RAT (N = 4) (PRIME WITH 60 μg OF ESTRADIOL FOR 3 DAYS)

| | 2h | 4h | 2h(BLOCK)[1] | 2h* |
|---|---|---|---|---|
| BLOOD | 0.033 ± 0.0059 | 0.045 ± 0.0003 | 0.048 ± 0.0066 | 0.033 ± 0.0109 |
| LIVER | 4.540 ± 0.5053 | 4.205 ± 0.4397 | 4.451 ± 1.1559 | 3.849 ± 0.4069 |
| KIDNEY | 0.742 ± 0.0756 | 0.796 ± 0.0300 | 0.742 ± 0.1451 | 0.530 ± 0.0752 |
| UTERUS | 0.426 ± 0.0177 | 0.400 ± 0.0312 | 0.297 ± 0.0356 | 0.248 ± 0.0535 |
| MUSCLE | 0.151 ± 0.0203 | 0.183 ± 0.0015 | 0.145 ± 0.0446 | 0.109 ± 0.0218 |
| BONE | 0.653 ± 0.1348 | 0.802 ± 0.0556 | 0.576 ± 0.1268 | 0.644 ± 0.0656 |
| INTESTINE | 0.917 ± 0.3058 | 1.101 ± 0.5986 | 0.742 ± 0.458 | 0.504 ± 0.1784 |
| UTERUS/BLOOD | 13.5 ± 2.97 | 9.1 ± 1.34 | 6.3 ± 1.62 | 6.6 ± 0.29 |
| UTERUS/MUSCLE | 2.9 ± 0.43 | 2.2 ± 0.16 | 2.2 ± 0.62 | 2.5 ± 0.37 |

[1]Rats were coinjected with estradiol (30 μg) and F-18 tracer in the blocked group.
*Without prime with estradiol (control); rats weighted about 175 gm.

The uterus to blood ratio at 2 h in rats without priming with estradiol group was 6.6±0.29, which changed to 13.5±2.97 in rats primed with estradiol. This increased uptake was blocked by coinjection of estradiol and $^{18}F$-tracer, where the ratio was 6.3±1.62. The data suggest that the uterus uptake by $^{18}F$-fluoro analogue of tamoxifen is mediated by an estrogen receptor process.

PROPHETIC EXAMPLE 17

Proposed Human Use of Alkyl Halogenated Tamoxifen and Derivatives as Ligands for Imaging Estrogen Receptor Positive Tumors The present prophetic example is provided to outline a procedure for the potential utility of the disclosed tamoxifen analogs in imaging estrogen-receptor positive tumor cells in humans. More specifically, the present prophetic example is aimed at outlining a method by which the described lower alkyl halo tamoxifen derivatives molecules may be used to image estrogen receptor positive tumors in vivo, most particularly those which typically occur in breast tissue and uterine tissue.

In a most preferred embodiment of the proposed method, the lower alkyl halotamoxifen derivative, trans-N,N-diethylfluoromethyltamoxifen (compound VI), trans N,N-dieththyl iodomethyltamoxifen (compound X), or bromomethyltamoxifen are the radiopharmaceuticals of choice to be used as the estrogen receptor imaging agent in a standard PET (positron emission tomography) and SPECT analysis. Of these, bromomethyltamoxifen produced the most superior results in animal studies presented by the Inventors.

The procedure for conducting estrogen receptor mapping would be substantially the same as that outlined by Minton et al.[4] The most significant modification of this procedure, among others, is that the estradiol-based derivatives described by Minton would not be used, and instead the aliphatic chain substituted tamoxifen derivatives of the claimed invention would be used.

Briefly stated, the most preferred method for imaging estrogen receptors in breast tumor tissue of a patient, wherein a radiolabeled alkyl-halogenated tamoxifen derivative (such as N,N-diethyl[$^{18}$F]fluoromethyltamoxifen, N,N-diethyl [$^{131}$I]iodomethyltamoxifen, N,N-diethylcloromethyltamoxifen or N,N-diethylbromomethyltamoxifen) is employed as the imaging agent, comprises the following steps: administering to the patient a sufficient amount (about 10 mCi) of radiolabeled alkyl-halogenated tamoxifen derivative to the breast tissue of the patient. The patient is then to be placed in a supine position in the PET device, at which time an emission scan of the chest at the level of the breast mass is to be performed. The technique for performing an emission scan of the chest is well known to those of skill in the art, and the general procedure for this technique is described by Mintun et al.,[4] which reference is specifically incorporated herein for this purpose.

Most preferably, the emission consecutive transaxial scan is to be performed for a 15 minute duration and most preferably about 110 minutes after the injection of the radiolabeled alkyl halogenated tamoxifen derivative. Most preferably, the tumor location is to be confirmed by palpation of the tissue after the patient is in the described supine position. The μCi/ml/pixel of tumor uptake will then be determined.

The PET images obtained are then to be evaluated for the presence or absence of focally increased uptake of the radiolabeled alkyl halogenated tamoxifen fluorotamoxifen ligand in the breasts and in the axillae as these were included in the field of view of the PET scanner. Those sites determined from the PET images to have demonstrated potential uptake are to be designated as accordingly abnormal foci uptake of the radiolabeled alkyl halogenated tamoxifen derivative.

The most preferred radiolabeled alkyl halogenated tamoxifen derivative to be used in the mapping and imaging of estrogen receptors in human tissue is N,N-diethylbromomethyltamoxifen.

PROPHETIC EXAMPLE 18

Proposed use of Alkyl Halogenated Tamoxifen and Derivatives in Treating Cancer The present prophetic example is provided to outline a procedure which could be employed for the potential utility of the described alkyl-halogenated tamoxifen derivatives in a treatment regimen for cancer in an animal.

While all of the aliphatic chain substituted tamoxifen derivatives described herein are expected to be useful in an animal treatment regimen, the lower alkyl halotamoxifen derivatives are most preferred. Among the lower alky halogen tamoxifen derivatives described herein, N,N-diethylfluoromethyltamoxifen is most particularly preferred.

The methods are postulated to be effective in the treatment of cancers which are estrogen-receptor positive, such as estrogen receptor positive breast cancers. The frequency and dosage amount of the disclosed tamoxifen derivates would be optimized according to standard techniques, which are well known to those skilled in the art.

The following references are specifically incorporated herein by reference in pertinent part for the reasons indicated herein.

BIBLIOGRAPHY

1. T. Nogrady (1985), *Medicinal Chemistry: A Biochemistry Approach*, Oxford University Press, New York, pp. 210–19.
2. Robertson et al. (1982), *J. Org. Chem.*, 47:2387–93.
3. Kallio et al. (1986), *Cancer Chemother Pharmacol.*, 17:103–8.
4. Mintun et al. (1988), *Radiology*, 169:45–8.
5. Hamacher et al. (1986), *J. Nucl. Med.* 27(2):235–8.
6. Foster et al. (1986), *Anticancer Drug Design*, 1:245–57.
7. Still et al. (1978), *J. Orn. Chem.*, 43:2923–4.
8. Foster et al. (1985), *J. Med. Chem.*, 28:1491–7.
9. Wieland et al. (1988), *Int. Rad. J. Appl. Instrum.* [A], 39:1219–25.
10. J. H. Fishman (1983), *Biochem. Biophys. Res. Commun.*, pp. 713–18.
11. McCague et al (1988), *J. Med. Chem.*, 31:1285–90.
12. Lowry et al. (1951), *J. Biol. Chem.*, 193:265–75.
13. U.S. Pat. No. 4,839,155—McCague (1989)
14. U.S. Pat. No. 3,288,806—Dewald (1966)
15. Allen et al. (1980), *British Journal of Pharmacology*, 71:83–91.
16. Pomper et al. (1988), *J. Med. Chem.* 31(7):1360–63.
17. Kiesewetter et al. (1984), *J. Organ. Chem.*, 49:4900.
18. Fur et al. (1984), *Pharmac. Ther.*, 25:127.
19. Kiesewetter et al. (1984) *J. Nocl. Med.*, 25:1212–1221.
20. Hochberg, (1979) *Science*, 205:1138–1140.
21. Katzenellenbogen et al. (1981), *J. Nucl. Med.*, 22:42–97.
22. Shani et al. (1985) *J. Med. Chem.*, 28:1504–1511.
23. Hanson et al. (1982), *Int. J. Nucl. Med. Biol.*, 9:105–107.
24. Kallio et al (1986) *Cancer Chemotherapy and Pharmacology*, 17:103–108.
25. Kuroda et al (1985) *J. Med. Chem*, 28:1497–1503.

26. DeGregorio et al (1987) *Cancer Chemother Pharmacol.,* 20:316–318.
27. Yang et al (1991) *Pharmaceutical Reseacrh,* 8(2):174–177.
28. Ram et al (1989) *Journal of Labelled Compounds and Radiopharmaceuticals,* 27(6):601–668.
29. Katzenellenbogen et al (1984) *Cancer Research,* 44:112–119.
30. Robertson et al (1982) *J. Org. Chem.* 47:2387–2393.
31. DeGregorio et al (1989) *Cancer Chemother. Pharmacol.,* 23:6870.
32. Kangas et al (1986) *Cancer Chemother. Pharmacol.,* 17:109–113.
33. Foster et al (1985) *J. Med. Chem.,* 28 (10):1491–1497.
34. Armstrong (1987) *J. of Chromatography,* 414:192–196.
35. Lien et al (1987) *Clin. Chem.,* 33(9):1608–1614.
36. Mosman, T. (1983) *J. Immunol. Methods.* 65:1608–1614.
37. Salituro et al (1986) *Steroids,* 48(5–6):287–313.
38. Shani et al (1985) *J. Med. Chem.,* 28:1504–1511.

What is claimed is:

1. A method for imaging estrogen receptors in an estrogen receptor-rich tissue of a patient comprising labeling the estrogen receptor with a radiolabeled lower alkyl-halo aliphatic chain substituted tamoxifen derivative comprising the steps of:
   administering a sufficient quantity of the radiolabeled lower alkyl-halo aliphatic chain substituted tamoxifen derivative to an estrogen receptor rich tissue of the patient;
   positioning the patient supine in a PET device;
   performing an emission scan of the estrogen-receptor rich tissue, and obtaining a PET image of the tissue; and
   evaluating the PET image for the presence or absence of focally increased uptake of the radiolabel in the tissue.

2. The method of claim 1 wherein the radio labeled lower alkyl halo aliphatic chain substituted tamoxifen derivative is trans-(18-F) fluoromethyldiethyltamoxifen.

3. The method of claim 1 wherein the radiolabeled lower alkyl halo aliphatic chain substituted tamoxifen derivative is 131-I iodomethyl N,N-diethyltamoxifen.

4. The method of claim 1 wherein the radiolabeled lower alkyl halo aliphatic chain substituted tamoxifen derivative is $^{77}$Br bromomethyl N,N-diethyltamoxifen.

5. The method of claim 1 wherein the radiolabeled lower alkyl halo aliphatic chain substituted tamoxifen derivative is $^{131}$I iodomethyltamoxifen.

6. The method of claim 1 wherein the radiolabeled lower alkyl halo aliphatic chain substituted tamoxifen derivative is chloromethyltamoxifen.

7. The method of claim 1 wherein the radiolabeled lower alkyl halo aliphatic chain substituted tamoxifen derivative is $^{77}$Br bromomethyltamoxifen.

8. The method of claim 1 wherein the estrogen receptor-rich tissue is breast tissue.

9. The method of claim 1 wherein the emission scan is performed for between about 15 minutes following administration of the alkyl-halogenated tamoxifen derivative.

10. The method of claim 1 wherein the emission scan is performed about 110 minutes after the administration of the alkyl-halogenated tamoxifen derivative.

* * * * *

UNITED STATES PATENT AND TRADEMARK OFFICE
CERTIFICATE OF CORRECTION

PATENT NO. : 5,192,525
DATED : March 9, 1993
INVENTOR(S) : Yang et al

It is certified that error appears in the above-indentified patent and that said Letters Patent is hereby corrected as shown below:

In claim 2, line 9, column 30, delete "trans" and insert therefor --trans--.

Signed and Sealed this

Twenty-eighth Day of December, 1993

Attest:

BRUCE LEHMAN

Attesting Officer

Commissioner of Patents and Trademarks